(12) United States Patent
McNulty et al.

(10) Patent No.: US 11,227,667 B2
(45) Date of Patent: Jan. 18, 2022

(54) USE OF A GUT MICROBIOME AS A PREDICTOR OF ANIMAL GROWTH OR HEALTH

(71) Applicant: Matatu, Inc., Washington, DC (US)

(72) Inventors: Nathaniel McNulty, Saint Louis, MO (US); Jeffrey I. Gordon, St. Louis, MO (US); Andrew C. Serazin, Washington, DC (US)

(73) Assignee: Matatu, Inc., Washington, DC (US)

( * ) Notice: Subject to any disclaimer, the term of this patent is extended or adjusted under 35 U.S.C. 154(b) by 760 days.

(21) Appl. No.: 15/324,471

(22) PCT Filed: Jul. 7, 2015

(86) PCT No.: PCT/US2015/039429
§ 371 (c)(1),
(2) Date: Jan. 6, 2017

(87) PCT Pub. No.: WO2016/007544
PCT Pub. Date: Jan. 14, 2016

(65) Prior Publication Data
US 2017/0220731 A1 Aug. 3, 2017

Related U.S. Application Data

(60) Provisional application No. 62/023,629, filed on Jul. 11, 2014.

(51) Int. Cl.
| | | |
|---|---|---|
| *G01N 33/48* | (2006.01) | |
| *G16B 20/20* | (2019.01) | |
| *G16B 20/00* | (2019.01) | |
| *G16B 40/00* | (2019.01) | |
| *G16B 50/00* | (2019.01) | |
| *G16B 50/30* | (2019.01) | |
| *C12Q 1/6869* | (2018.01) | |
| *C12Q 1/689* | (2018.01) | |

(52) U.S. Cl.
CPC .......... *G16B 20/20* (2019.02); *C12Q 1/6869* (2013.01); *G16B 20/00* (2019.02); *G16B 40/00* (2019.02); *G16B 50/00* (2019.02); *G16B 50/30* (2019.02); *C12Q 1/689* (2013.01); *C12Q 2600/124* (2013.01)

(58) Field of Classification Search
None
See application file for complete search history.

(56) References Cited

U.S. PATENT DOCUMENTS

| 6,996,472 B2 | 2/2006 | Wilkes et al. | |
| 8,642,839 B2 | 2/2014 | Azhakanandam | |
| 8,775,092 B2 | 7/2014 | Colwell et al. | |
| 9,881,135 B2 * | 1/2018 | Backhed | G16H 50/20 |
| 2009/0291858 A1 | 11/2009 | Andersen | |
| 2011/0206654 A1 | 8/2011 | Hodin et al. | |
| 2013/0225439 A1 * | 8/2013 | Princen | C12Q 1/6883 506/9 |
| 2013/0337456 A1 | 12/2013 | Sequenom | |
| 2014/0045744 A1 * | 2/2014 | Gordon | C12Q 1/025 514/5.7 |
| 2014/0136120 A1 * | 5/2014 | Colwell | G16B 40/00 702/20 |
| 2016/0244839 A1 * | 8/2016 | Fricke | C12Q 1/6883 |

OTHER PUBLICATIONS

Bursel MK et al. "Functional Genomic and Metabolic Studies of the Adaptations of a Prominent Adult Human Gut Symbiont, Bacteroides thetaiotaomicron, to the Suckling Period," (2006) J Biol Chem 281:36269-71.

Cantarel BL et al. "The Carbohydrate-Active EnZymes database (CAZy): an expert resource for Glycogenomics," (2009) Nucleic Acids Res 37:D233-238.

Desantis TZ et al., "High-Density Universal 16s rRNA microarray reveals broader diversity in samples than clone library," 2007, Microbiol Ecol 53:371-383.

Guo F et al. "Taxonomic Precision of Different Hypervariable Regions of 16S rRNA Gene and Annotation Methods for Functional Bacterial Groups in Biological Wastewater Treatment," PLOS One 8(10) e76185, Oct. 2013, 11 pages.

Hamady M et al. "Microbial community profiling or human microbiome projects: Tools, techniques, and challenges," Genome Res. 19 pp. 1141-1152, 2009.

International Search Report and Written Opinion issued on PCT/US2015/039429, dated Oct. 1, 2015.

Saier MH "A Functinal-Phylogenetic Classification System for Transmembrane Solute Transporters," Microbiol Mol Biol Rev 64 (2): 354-411, Jun. 2000.

Soergel D. et al., "Selection of primers for optimal taxonomic classification of environmental 16S rRNA gene sequences," ISME Journal 6, pp. 1440-1444, 2012.

Wilson KH et al, "High-density microarray of small sub-unit ribosomal DNA Probes," 2002, Appl Environ Microbiol 68: 2535-2541.

Karlsson et al, "Gut metagenome in European women with normal, impaired and diabetic glucose control—Supplementary Information," Nature, May 29, 2013, pp. 1-25.

Karlsson et al, "Gut metagenome in European women with normal, impaired and diabetic glucose control" Nature, vol. 498, No. 7542 May 29, 2013, pp. 99-103.

Pan et al., "Intestinal microbiome of poultry and its interaction with host and diet," Gut Microbes, vol. 5, No. 1, Oct. 31, 2013, pp. 108-119.

(Continued)

Primary Examiner — Anna Skibinsky

(74) Attorney, Agent, or Firm — Foley & Lardner LLP

(57) ABSTRACT

The present technology encompasses systems for predicting a characteristic of an individual subject, as well as methods for predicting a characteristic of a particular subject based on the systems of the technology disclosed herein. The disclosure herein also provides methods to improve a characteristics in a subject, based on the prediction produced by the system.

14 Claims, 12 Drawing Sheets

(56) References Cited

OTHER PUBLICATIONS

Ross et al. "Metagenomic Predictions: From Microbiome to Complex Health and Environmental Phenotypes in Humans and Cattle," PLOS ONE, vol. 8, No. 9, Sep. 4, 2013, p. E73056.
Search Report issued on European Application 15818902.7, dated Mar. 2, 2018.
Singh et al., "Taxonomic and gene-centric metagenomics of the fecal microbiome of low and high feed conversion ratio (FCR) broilers," Journal of Applied Genetics, vol. 55, No. 1, Oct. 18, 2013, pp. 145-154.
European search report issued for EP App. No. 15818902.7, dated Jul. 2, 2018.
Lamendella et al., Comparative fecal metagenomics unveils unique functional capacity of the swine gut, BMC Microbiology 2011, 11:103, pp. 1-17.
Torok et al., Identification and characterization of potential performance-related gut microbiotas in broiler chickens across various feeding trials, Applied and Environmental Microbiology, vol. 77, No. 17, Sep. 2011, p. 5868-5878.
Examination Report in EP Patent Application No. 15/818902.7 dated Apr. 22, 2020 (13 pages).
Karlsson, et al., "Gut metagenome in European women with normal, impaired and diabetic glucose control—Supplementary Information," Nature, May 29, 2013, pp. 1-25, XP055451421, DOI: 10.1038/nature12198.

\* cited by examiner

USE OF A GUT MICROBIOME AS A
PREDICTOR OF ANIMAL GROWTH OR
HEALTH

CROSS-REFERENCE TO RELATED
APPLICATIONS

This application is a U.S. National Stage of PCT/US2015/039429 filed Jul. 7, 2015, which claims the benefit of and priority to U.S. Provisional Application No. 62/023,629, filed Jul. 11, 2014, the contents of which are hereby incorporated by reference in their entireties.

BACKGROUND

DNA sequencing technology allows the collection of high-dimensional data from microbial communities on an unprecedented scale. It is well known in the art that the composition of microbial communities varies between subjects of the same species, as well as across species. A major goal of recent research has been the identification of important groups of microorganisms that vary according to physiological or disease states in the host at the time the sample was taken. It is generally accepted that the phylogenetic composition of gut bacterial communities of an animal changes over time from birth through adulthood. In humans, this progression results in an adult-like configuration within the three-year period after birth. In swine, a dramatic change in the community structure of the gut microbiome from 10 to 22 weeks has been shown. During adulthood a state of quasi-equilibrium is reached that persists over time in a healthy individual. Across populations of individuals, there is significant variation driven by many factors including environmental determinants such as diet, infectious disease exposure, and genetics. Analyses of microbiota structure and function relate to stratification of current phenotypes or characteristics (e.g. obesity or obesity-related disorders). There remains a need in the art to make predictions of future characteristics (e.g., probability of specific parameters of health and disease in the future) based on the structure or function of gut microbiota.

SUMMARY

In one aspect the present disclosure provides a system for identifying a discriminatory microbial nucleic acid feature, the system comprising: (a) a database comprising: (i) a first data set, the first data set comprising a plurality of microbial nucleic acid features for each of a plurality of subjects, wherein (1) each of the plurality of subjects are of the same species, and (2) there is inter-subject variability in the nucleic acid features; (ii) a second data set, the second data set comprising at least one measurement of at least one characteristic for each subject from step (i) and a defining relationship between each characteristic measurement and the subject, wherein there is inter-subject variability in the measured characteristic of each subject; (b) at least one processor; and (c) a learning application executed by the at least one processor to: (i) process the first data set and the second data set to identify inter-subject variation in the nucleic acid features of the first data set that relate to inter-subject variation in the characteristic measurements in the second data set; and (ii) identify microbial nucleic acid features that positively or negatively discriminate a characteristic.

In some embodiments, the nucleic acid features comprise microbial taxonomic information, microbial functional information, or a combination thereof.

In some embodiments, the nucleic acid features are microbial taxonomic information.

In some embodiments, the learning application is a random forest learning algorithm.

In some embodiments, the learning algorithm performs a classification analysis or a regression analysis.

In some embodiments, the taxonomic information is determined from at least about 5,000 sequence reads.

In some embodiments, the characteristic is selected from the group consisting of average daily gain, weight, body composition, and feed conversion efficiency.

In some embodiments, the second data set further comprises one or more additional characteristics and the model can predict multiple future characteristics.

In some embodiments, the database further comprises an additional data set, the additional data set comprising an additional characteristic measurement for each subject included in the first data set; and the learning application processes the first data set, the second data set and the one or more additional data sets to identify inter-subject variation in the nucleic acid features of the first data set and the one or more additional data sets that relate to inter-subject variation in the characteristic measurements in the second data set.

In one aspect the present disclosure provides a method for predicting a characteristic in a subject, the method comprising (a) using a system described herein to identify microbial nucleic acid features that positively differentiate a characteristic to be predicted; selecting a set comprising a plurality of microbial nucleic acid features from step (a), wherein the set can be used to create a predictive model defining the relationship between the features of the set and the characteristic; (b) determining the features in the set of step (a) in a subject, wherein the subject is of the same species as the subjects comprising the database of step (a) of claim 1; and (c) applying the predictive model to the subject's nucleic acid features to predict the characteristic.

In some embodiments, at least 3 nucleic acid features are selected in step (b).

In some embodiments, the nucleic acid feature is microbial taxonomic information.

In one aspect the present disclosure provides a method for predicting a future characteristic of a particular subject, the method comprising: (a) retrieving a first data set and a second data set from a database, wherein: (i) the first data set comprises a plurality of microbial nucleic acid features of gut microbiota for each of a plurality of subjects, wherein each of the plurality of subjects are the same species, and there is inter-subject variability in the microbial nucleic acid features; (ii) the second data set comprises at least one measurement of a characteristic for each of the plurality of subjects and identifies a relationship between the characteristic measurement and each subject, and wherein there is inter-subject variability in the measured characteristic of each subject; (b) processing the first data set and the second data set using at least one processor to identify a first inter-subject variation in the first data set that impacts a second inter-subject variation in the second data set and (c) identifying microbial nucleic acid features that positively or negatively discriminate a characteristic impact model positive performance at the at least one processor based on the first inter-subject variation identified and the second inter-subject variation identified; (d) defining a predictive model at the at least one processor, the predictive model defining a relationship between the discriminatory microbial nucleic acid features and the characteristic; and (e) applying the predictive model to nucleic acid features of the particular subject at the at least one processor to predict at least one particular characteristic of that particular subject; and (f) generating a predictive result, at the at least one processor, for display, the predictive result comprising at least one particular characteristic for the particular subject.

In one aspect the present disclosure provides a method for predicting the occurrence of a characteristic in an animal subject from a nucleic acid sample of the microbial community in the gastrointestinal tract of the animal subject, comprising identifying in the nucleic acid sample the occurrence of at least 3 nucleic acid features of the gut microbiota, wherein the occurrence of the at least 3 features are indicative of the occurrence of the characteristic.

In some embodiments, the characteristic is selected from the group consisting of average daily gain, weight, and feed conversion efficiency.

In some embodiments, the gut microbiota sample is a fecal sample.

In some embodiments, the subjects are swine.

In some embodiments, the discriminatory taxonomic features are a group of at least three OTUs.

In some embodiments, step (a) further comprises retrieving an additional data set from a database, the additional data set comprising an additional characteristic measurement for each subject included in the first data set; and step (b) further comprises processing the first data set, the second data set and the one or more additional data sets at least one processor to identify inter-subject variation in the nucleic acid features of the first data set and the one or more additional data sets that relate to inter-subject variation in the characteristic measurements in the second data set.

In one aspect the present disclosure provides a method of managing an animal growing operation or an animal processing operation, comprising: (a) predicting a future characteristic for two or more animals, and (b) sorting, selecting or ranking the two or more animals into one or more groups based on the similarity of the future characteristic, and wherein animals in different groups will be managed differently in order to optimize the future characteristic.

In some embodiments, the characteristic relates to performance of the offspring of the plurality of subjects.

In some embodiments, the system further comprises determining a breeding index.

In some embodiments, characteristic relates to performance of the offspring of the subject.

In some embodiments, the method further comprises determining a breeding index.

DETAILED DESCRIPTION

Figure 1A:
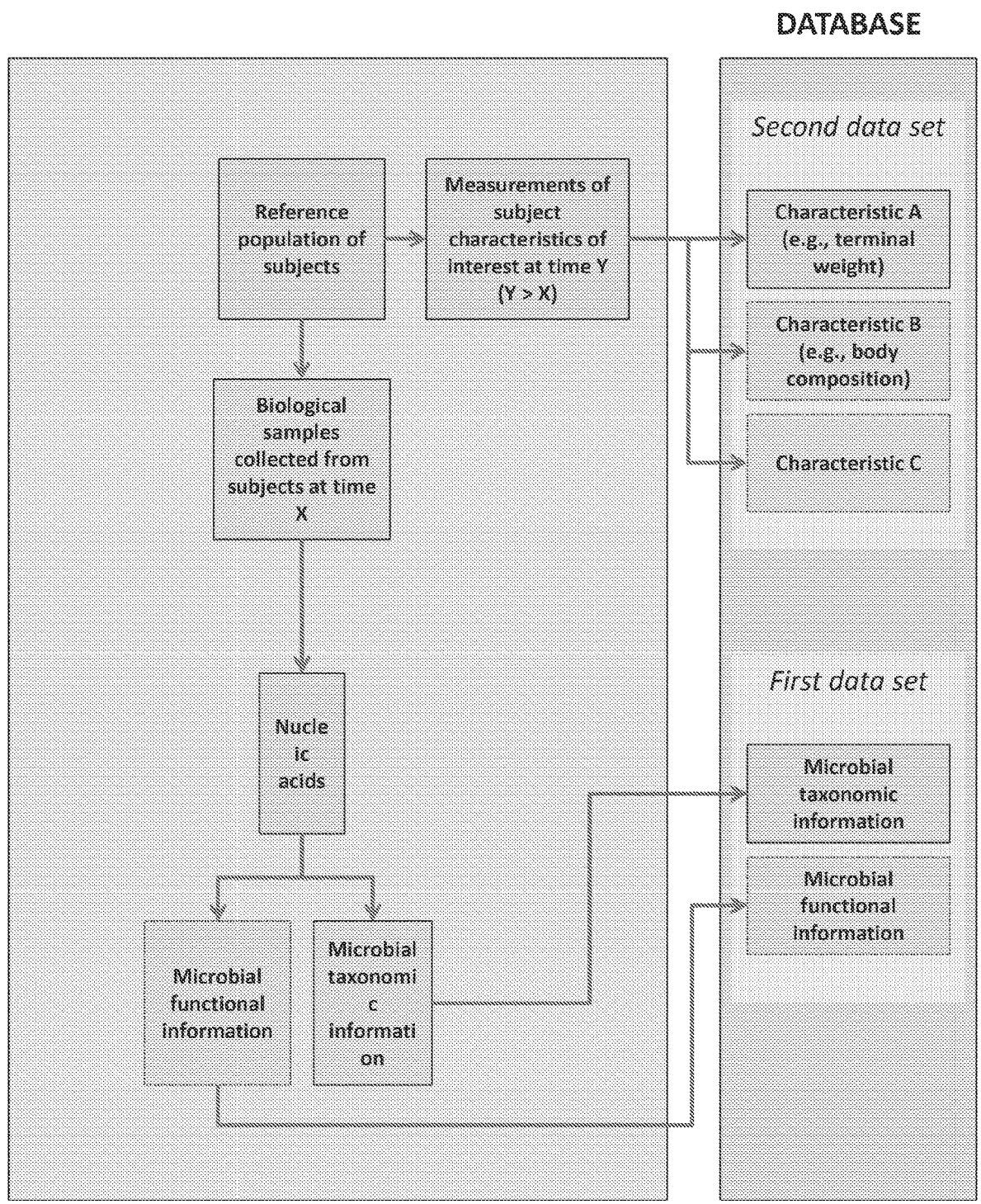
FIG. 1A, FIG. 1B, and FIG. 1C illustrate the flow of information through a system of the present technology.

The disclosure described herein provides systems for predicting a characteristic of an individual subject, as well as methods for predicting a characteristic of a particular subject based on the systems disclosed herein. The disclosure herein also provides methods to improve a characteristic in a subject, based on the prediction produced by the system. The disclosure also provides a system for assessment of specific patterns of microbial abundance in the early life of animals and using this assessment to make predictions about future phenotypic traits or characteristics. The disclosure further provides methods to select animals predicted to have specific traits for use in breeding. Various aspects of the disclosure are described in further detail in the following sections.

I. Systems for Predicting a Characteristic

One aspect of the disclosure provides a system for predicting at least one characteristic of an individual subject. For example, a system of the present technology may predict at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more characteristics of an individual subject. A system may comprise a database, at least one processor, and a learning application executed by the at least one processor. Optionally, a system may further comprise a data acquisition device.

The term "subject," as used herein, refers to any animal with a gut microbiota. Preferred subjects include, but are not limited to, animals with a monogastric digestive system, animals with a ruminant digestive system, animals with an avian digestive system, and fish. Included within the definition of monogastric animal are hind-gut fermenters. Non-limiting examples of monogastric animals may include cats, dogs, horses, humans, non-human primates, swine, rabbits, and rodents. Suitable swine include, but are not limited to, pigs, hogs, and boars. Non-limiting examples of avians may include poultry. Suitable poultry include, but are not limited to chickens, geese, ducks, turkeys, quail, Guinea fowl and squab. Non-limiting examples of ruminants include cattle, deer, goat, sheep, llama, alpaca, yaks, reindeer, and caribou. Non-limiting examples of fish may include salmonids, tilapia, catfish, sea bass, bream, tuna, mollusks, and crustaceans. Suitable salmonids include, but are not limited to, salmon, steelhead, and carp. Suitable mollusks include, but are not limited to, mussels, clams, oysters, and scallops. Suitable crustaceans include, but are not limited to, shrimp, prawns, crayfish, lobsters, and crabs. In certain embodiments, a subject is a production animal.

The terms "gut microbial community" and "gut microbiota", as used herein, are interchangeable and refer to microbes that have colonized and inhabit the gastrointestinal tract of a subject. While various aspects of the present technology are exemplified with bacteria, the technology is applicable to all microbes including, but not limited to, archaea, bacteria, fungi, protists and viruses. Contemplated within the scope of the technology are viruses of archaea, bacteria, fungi, protists, as well as viruses of a subject. A subject's gut microbiota may be naturally acquired or artificially established. Means by which a subject naturally acquires its gut microbiota are well known. Such examples may include, but are not limited to, exposure during birth, environmental exposure, consumption of foods, and coprophagy. Means by which a subject's gut microbiota may be artificially established are also well known. For example, artificially established gut microbial communities can be established in gnotobiotic animals by inoculating an animal with a defined or undefined consortium of microbes. Typically, a naturally acquired gut microbiota is comprised of both culturable and unculturable components. An artificially acquired gut microbiota may be similarly comprised of both culturable and unculturable components, or may consist of only culturable components. The phrase "culturable components" refers to the microbes comprising the gut microbiota that may be cultured in vitro using techniques known in the art. Culture collections of gut microbial communities are described in detail in PCT/US2012/028600, incorporated herein in its entirety by reference. A subject's existing gut microbiota may also be modified or manipulated, for example, by administering one or more isolated microbial species, dietary supplements, or changing the subject's diet.

Other aspects are described in further detail below.

A. Data Acquisition Component

A data acquisition component uses a sample comprising a plurality of heterogeneous nucleic acids produced by a subject's gut microbiota (i.e. "a nucleic acid sample") as an input and produces as an output a plurality of microbial nucleic acid features. When systems of the technology comprise a data acquisition component, the output of the data acquisition component is an input for a database of the system.

A microbial nucleic acid feature refers to a measurement of the amount of a nucleic acid in a nucleic acid sample that is either qualitative (present/absent) or quantitative (abundance of a nucleic acid). A taxonomic assignment and/or a functional assignment may also be provided to a nucleic acid in a nucleic acid sample by a program/utility of a data acquisition component according to methods known in the art, and/or as detailed herein. As such, the term "microbial nucleic acid feature" also refers to the presence, absence and/or abundance of a nucleic acid assigned a taxonomic classification in a nucleic acid sample (i.e. microbial taxonomic information), and the presence, absence and/or abundance of a nucleic acid assigned a functional classification in a nucleic acid sample (i.e. "microbial functional information").

Generally speaking, a suitable nucleic acid used for taxonomic classification is universally distributed among the gut microbial population being queried allowing for the analysis of phylogenetic relationships among distant taxa, and has both a conserved region and at least one region subject to variation. The presence of at least one variable region allows sufficient diversification to provide a tool for classification, while the presence of conserved regions enables the design of suitable primers for amplification (if needed) and/or probes for hybridization for various taxa at different taxonomic levels ranging from individual strains to whole phyla. While any suitable nucleic acid known in the art may be used, one skilled in the art will appreciate that selection of a nucleic acid or region of a nucleic acid to amplify may differ by environment. In some embodiments, a nucleic acid queried is a small subunit ribosomal RNA gene. For bacterial and archaeal populations, at least the V1, V2, V3, V4, V5, V6, V7, V8 and/or V9 regions of the 16s rRNA gene are suitable, though other suitable regions are known in the art. Guidance for selecting a suitable 16S rRNA region to amplify can be found throughout the art, including Guo F et al. PLOS One 8(10) e76185, 2013; Soergel D A W et al. ISME Journal 6: 1440, 2012; and Hamady M et al. Genome Res. 19:1141, 2009, each hereby incorporated by reference in its entirety. For protists, at least the SSU rRNA V9 hypervariable region is suitable. For fungi, at least the ITS region is suitable. Sequencing of viruses relies on filtration and shotgun sequencing of virus-like particles; no universal primers are available for amplification. Microbial taxa may be defined at any taxonomic level, including phyla, class, order, family, genus, species, strain, or a combination thereof. A skilled artisan will appreciate that while more resolved levels of taxonomy (e.g. genus, species or strain) may generally be more predictive, there may be circumstances where use of higher levels of taxonomy improves the performance of the system.

Suitable nucleic acids used for functional classification may include a nucleic acid that encodes a polypeptide which can be assigned to a functional group known in the art. The current technology is not limited to any one particle classification scheme. Without wishing to be bound by theory, suitable functional groups may include, but are not limited to, carbohydrate active enzymes (CAZymes), a polysaccharide utilization locus (PUL), a transmembrane solute transporter, a KEGG group, a COG group, an Enzyme Commission (EC) number, or their subgroups. Preferred functional groups include, but are not limited to, a CAZy enzyme class, a CAZy family, polysaccharide utilization loci (PULs), or ABC (ATP-binding cassette) importers. Methods for identifying functional groups are known in the art. For example, CAZymes and PULs are described in Cantarel B L et al. (2009) Nucleic Acids Res 37:D233-238) or Bursel M K et al. (2006) J Biol Chem 281: 36269-71. Transmembrane solute transporters, including ABC (ATP-binding cassette) importers, have been classified as described in Saier M H (2000) Microbiol Mol Biol Rev 64 (2): 354-411.

In some embodiments, an output is a qualitative measurement of the amount one or more of the nucleic acids in a nucleic acid sample. In other embodiments, an output is a quantitative measurement of the amount of one or more of the nucleic acids in a nucleic acid sample. In still other embodiments, an output is microbial taxonomic information for one or more of the nucleic acids in a nucleic acid sample. In yet other embodiments, an output is microbial functional information for one or more of the nucleic acids in a nucleic acid sample. An output of a data acquisition component may also be any combination of a qualitative or quantitative measurement, microbial taxonomic information, and microbial functional information.

A data acquisition component may produce a microbial nucleic acid feature by any method known in the art. For example, quantitate and qualitative measures of the abundance of a nucleic acid may be made by quantitative PCR, northern blot, or more preferably by sequencing-based methods or array-based methods.

1. Sample and Sample Processing

A suitable nucleic acid sample comprises a plurality of heterogeneous nucleic acids produced by a subject's gut microbiota. A preferred nucleic acid sample may be a nucleic acid sample obtained from a suitable fecal sample. Fecal samples are commonly used in the art to sample gut microbiota. Methods for obtaining a fecal sample from a subject are known in the art and include, but are not limited to, rectal swab, stool collection, and sampling of the floor or environment where animals defecate (e.g. a pen in a commercial animal farm). Suitable fecal samples may be freshly obtained or may have been stored under appropriate temperatures and conditions known in the art. Methods for extracting nucleic acids from a fecal sample are also well known in the art. The nucleic acids comprising the nucleic acid sample may or may not be amplified prior to being used as an input, depending upon the type and sensitivity of the data acquisition component. When amplification is desired, nucleic acids may be amplified via polymerase chain reaction (PCR) from a nucleic acid sample. Methods for performing PCR are well known in the art. Selection of nucleic acids or regions of nucleic acids to amplify are discussed above. The nucleic acids comprising the nucleic acid sample may also be fluorescently or chemically labeled, fragmented, or otherwise modified prior to sequencing or hybridization to an array as is routinely performed in the art.

2. Sequencing-Based Data Acquisition and Processing

Figure 8:
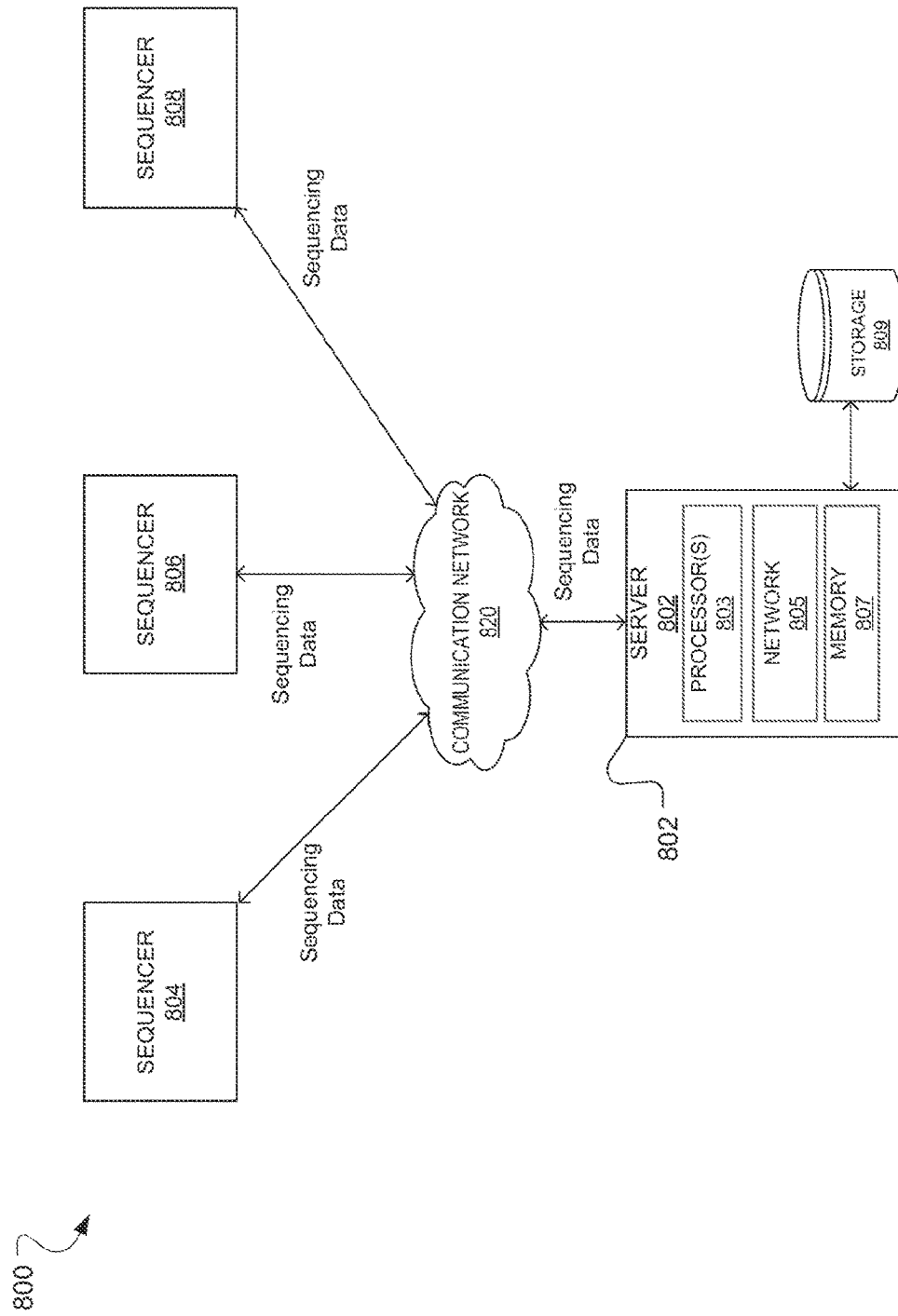
FIG. 8 provides an example computing architecture.

Referring to FIG. 8, a computing architecture and/or system 800 is provided for predicting at least one characteristic of an individual subject, according to one embodiment. The system 800 may be used to produce a microbial nucleic acid feature for use in determining a future characteristic of a subject. As illustrated, the computing architecture 800 includes a server 802, which may include one or more processors (CPUs) (e.g., a plurality of processors in a parallel processing environment), a memory 807, storage 809, and various network resources/components 805 of any suitable type. The server 802 may interact or otherwise communicate with one or more data acquisition components, depicted in the illustrated embodiments as sequencers 804, 806, and 808 that are capable of generating sequence data and/or sequencing data for use in producing a microbial nucleic acid feature. More particularly, the server 802 may receive or otherwise obtain sequencing data from the sequencers 804, 806, and 808 for use in determining a microbial nucleic acid feature. The present technology is not limited to any particular sequencing platform or sequencer. Suitable sequencing platforms are capable of single-molecule sequencing, ion semiconductor sequencing, pyrosequencing, sequencing by synthesis, sequencing by ligation, nanopore sequencing, or tunneling currents sequencing. In one embodiment, the sequencer 804, 806, and/or 808, may be a 454 sequencer, an Illumina sequencer, a MiSeq Desktop Sequencer, a NextSeq Sequencer, an Ion PGM™ sequencer, a MinION™ device, a GridION™ device, a Ion Proton™ device, and/or the like. The server 802 may communicate with the sequencers 804, 806, and/or 808 through a communications network 820, which may be the Internet, an intranet, a local area network, a wireless local network, a wide area network, or another communication network, as well as combinations of networks. Alternatively, the server 802 may communicate with the sequencers 804, 806, and/or 808 directly, such as via a wire-line connection. Sequence data from the sequencers 804, 806, and 808 may be used by a program to qualitatively or quantitatively determine the amount of a nucleic acid in a nucleic acid sample, as is known in the art. While the illustrated embodiment describes sequence data as being transmitted from the sequencers (e.g., the sequencers 804, 806, and 808) to the server 202, it is contemplated that the sequence data may come from elsewhere and/or already be located within the system, such as for example, pre-stored in the storage 809.

Sequence data from the sequencers 804, 806, and 808 may be used by a program to assign a taxonomic classification to a sequence read. Two general approaches have been widely pursued for binning sequence data into microbial taxa. The first method relies upon reference taxonomic outlines to classify individual sequence reads to taxonomic bins (i.e., a "phylotype-based method"). The second method allows the data to "speak for themselves" by assigning individual sequence reads to operational taxonomic units (OTUs) based on the similarity of sequences within a data set to each other. Only after sequences are grouped is a representative sequence selected and compared to a reference set. If a match is identified in the reference set, that OTU will be given an identity. Using an OTU-based approach, a suitable threshold for genus classification is that genus-level phylotypes share ≥90%, preferably ≥93%, even more preferably ≥95% identity over a given region. For example, a suitable threshold for genus classification is that genus-level phylotypes share 90%, 91%, 92%, 93%, 94%, 95% or more identity over a given region. A suitable threshold for species classification is that species-level phylotypes share ≥94%, preferably ≥97% identity over a given region. For example, a suitable threshold for species classification is that species-level phylotypes share 94%, 95%, 96%, 97% or more identity over a given region. A suitable threshold for species classification is that strain-level phylotypes share ≥97% identity over a given region. For example, a suitable threshold for strain classification is that strain-level phylotypes share 97%, 98%, 99% or more identity over a given region. The present technology is not limited to any particular software package. Suitable software packages include, but are not limited to, QIIME (Quantitative Insights Into Microbial Ecology; qiime.org), mothur (www.mothur.org), and MG-RAST (Metagenomics RAST; metagenomics.anl.gov).

Figure 1B:
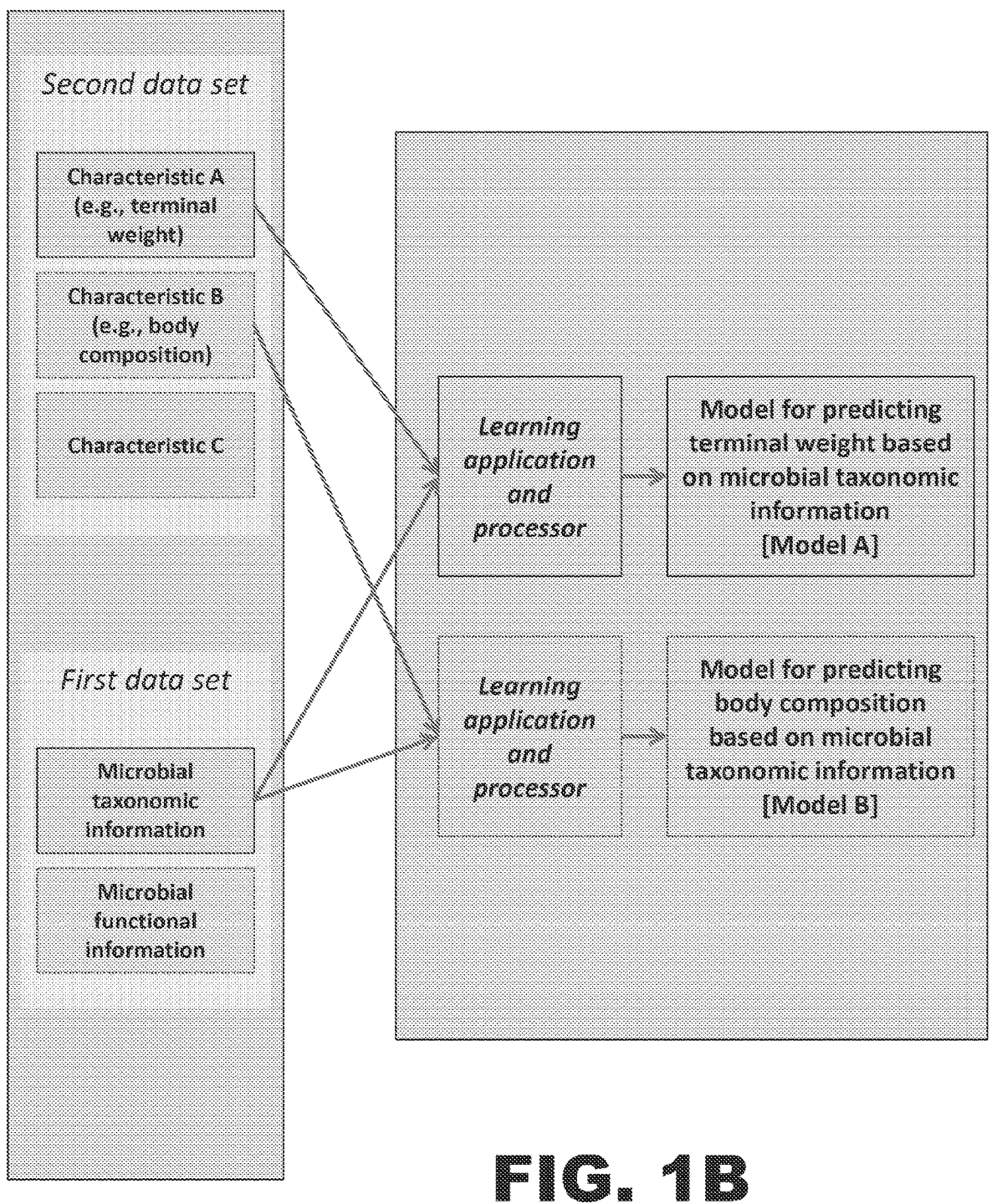
Figure 1C:
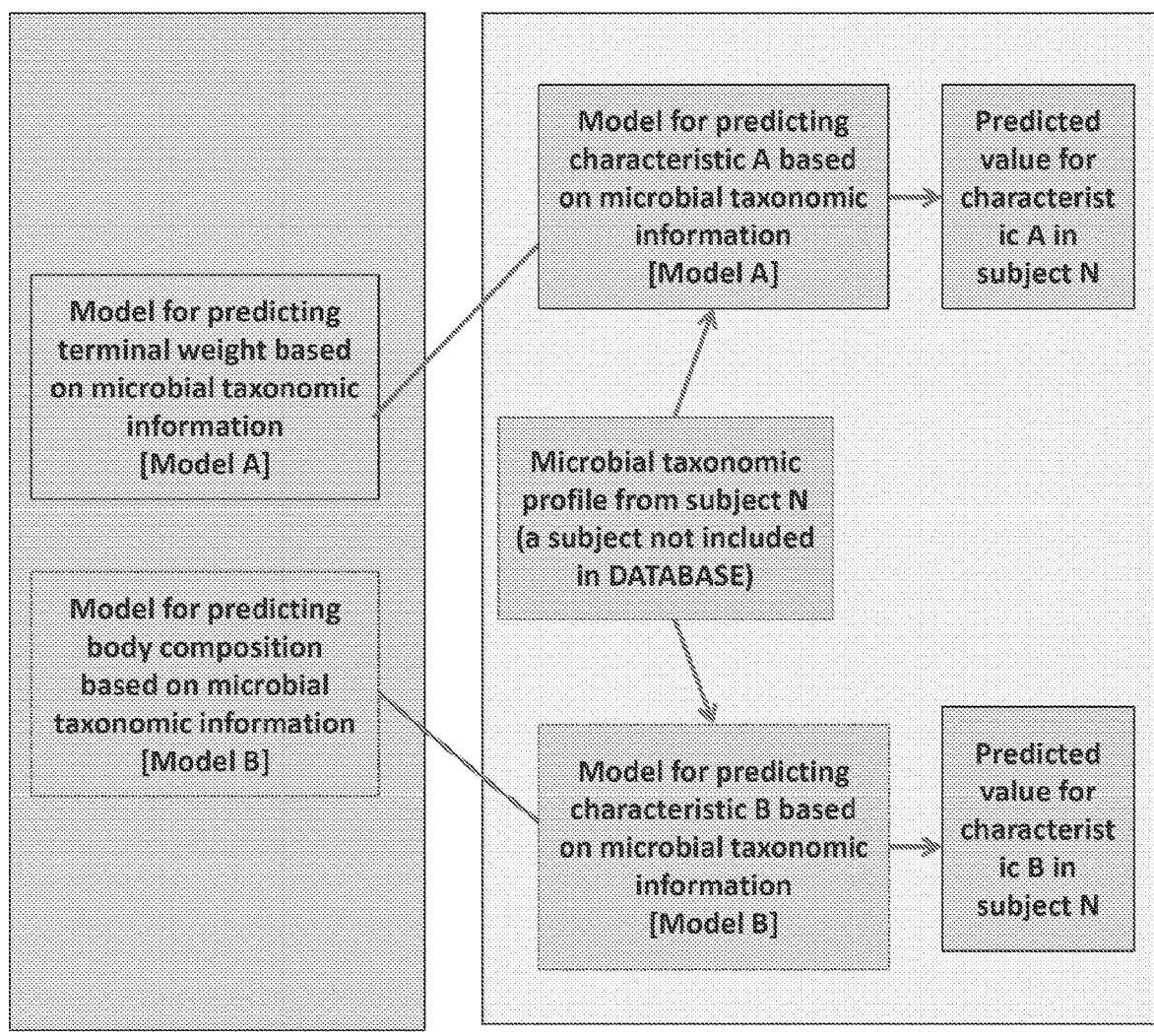

In some embodiments, an output is microbial taxonomic information for one or more of the nucleic acids in a nucleic acid sample, wherein a nucleic acid is assigned to a phylotype. In other embodiments, an output is microbial taxonomic information for one or more of the nucleic acids in a nucleic acid sample, wherein a nucleic acid is assigned to an OTU. In other embodiments, an output is microbial taxonomic information for one or more of the nucleic acids in a nucleic acid sample, wherein a nucleic acid is assigned to the closest taxonomic grouping such as phylum, class, family, order, genus, and species. Relative abundance of a species may be defined by the number of sequencing reads that can be unambiguously assigned to each microbial genome after adjusting for genome uniqueness. Microbial taxonomic information may be an input for a database of the system. Specifically, microbial taxonomic information produced by a data acquisition component may contribute to a first data set of a database of the system as depicted in FIG. 1.

Sequence data from the sequencers 804, 806, and 808 may be used by a program to assign a functional classification to a sequence read. Methods to functionally classify sequence reads are known in the art. Suitable functional groups may include, but are not limited to, carbohydrate active enzymes (CAZymes), a polysaccharide utilization locus (PUL), a transmembrane solute transporter, a KEGG group, a COG group, an Enzyme Commission (EC) number, or their subgroups. Preferred functional groups include, but are not limited to, a CAZy enzyme class, a CAZy family, polysaccharide utilization loci (PULs), or ABC (ATP-binding cassette) importers.

In some embodiments, an output is microbial functional information for one or more of the nucleic acids in a nucleic acid sample, wherein a nucleic acid is assigned to a CAZy enzyme class, a CAZy family, a PUL, a KEGG group, a COG group, or an Enzyme Commission (EC) number. Microbial functional information may be an input for a database of the system. Specifically, microbial functional information produced by a data acquisition component may contribute to a first data set of a database of the system as depicted in FIG. 1.

3. Array-Based Data Acquisition and Processing

Figure 9:
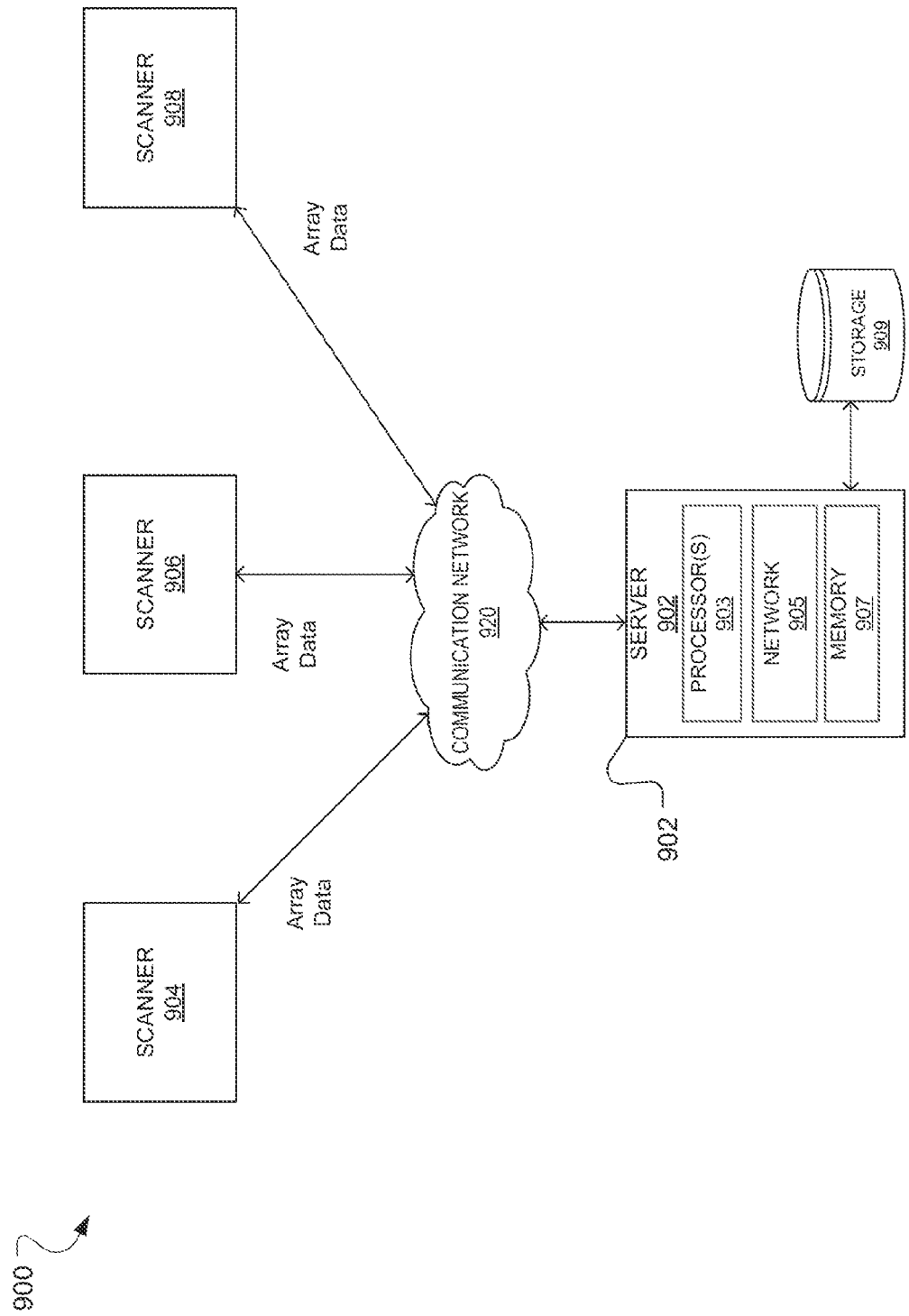
FIG. 9 provides an example computing architecture.

Referring to FIG. 9, a computing architecture and/or system 900 is provided for predicting at least one characteristic of an individual subject, according to one embodiment. The system 900 may be used to produce a microbial nucleic acid feature for use in determining a future characteristic of a subject. The computing architecture and/or system 900 includes a server 902, which may include one or more processors (CPUs) (e.g., a plurality of processors in a parallel processing environment), a memory 907, storage 909, and various network resources/components 905 of any suitable type. The server 902 may interact or otherwise communicate with one or more data acquisition components, depicted in the illustrated embodiments as one or more scanners 904, 906, and 908 that are capable of generating array data that captures the intensity of each position on the array for use in producing a microbial nucleic acid feature. More particularly, the server 902 may receive or otherwise obtain array data from the scanner 904, 906, and 908 for use in determining a microbial nucleic acid feature. The present technology is not limited to any particular array platform. In one embodiment, the scanner 904, 906, and/or 908, may be a GeneChip® Scanner and/or the like. The server 902 may communicate with the array imager 904, 906, and/or 908 through a communications network 920, which may be the Internet, an intranet, a local area network, a wireless local network, a wide area network, or another communication network, as well as combinations of networks. Alternatively, the server 902 may communicate with the scanners 904, 906, and/or 908 directly, such as via a wire-line connection. Array data from the scanners 804, 806, and 808 may be used by a program (e.g. a hybridization scoring algorithm) to interpret probe responses into reliable identifications, as is known in the art. While the illustrated embodiment describes array data as being transmitted from the scanners (e.g., the scanners 904, 906, and 908) to the server 202, it is contemplated that the array data may come from elsewhere and/or already be located within the system 900, such as for example, pre-stored within the storage 909.

An array-based data acquisition component also comprises an array, the array comprising multiple oligonucleotide probes arrayed onto a solid surface. An array may be commercially available or custom. In some embodiments, an array is a PhyloChip. In other embodiments, an array is a SNP Genotyping array. In other embodiments, an array is a GeneChip®.

For phylogenetic arrays, probes must be designed that are sensitive to only a specified branch of a taxonomic tree, but if a single unique probe for a taxon cannot be found, several probes can be utilized in combination with rules-based scoring. Increasing the total number of probes within a microarray allows more taxa to be queried and detection confidence can be improved. The absolute number of probes comprising a microarray can and will vary. For example, microbial taxonomic information has been accurately obtained using arrays with 62,358 probes, 297,851 probes, and 506,944 probes. See, for example, DeSantis, T Z, et al. (2005) Rapid quantification and taxonomic classification of environmental DNA from both prokaryotic and eukaryotic origins using a microarray. FEMS Microbiol Lett 245: 271-278; Wilson, K H et al. (2002) High-density microarray of small-subunit ribosomal DNA probes. Appl Environ Microbiol 68: 2535-2541; DeSantis, T Z, et al. (2007) 16s rRNA microarray reveals broader diversity in samples than clone library. Microbiol Ecol 53: 371-383; or US 20090291858. The design of a suitable phylogenetic array is further described in US 20090291858, hereby incorporated by reference in its entirety.

For gene expression arrays, probe sets may be designed to target all predicted coding genes within a gut microbiome or only a subset of predicted coding genes within a gut microbiome. A probe set for a gene expression array may also be designed to target one or more specific functional groups including, but not limited to, CAZymes, a polysaccharide utilization locus (PUL), a transmembrane solute transporter, a KEGG group, a COG group, an Enzyme Commission (EC) number, or their subgroups.

B. A Database of the System

A database of the system comprises at least two data sets. For example, a database of the system may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 or more data sets. Minimally, a database of the system comprises a first and a second data set, as depicted in FIG. 1, wherein a first data set comprises a microbial nucleic acid feature for each of a plurality of subjects collected at a first time ("time X" in FIG. 1), and a second data set comprises a characteristic measurement for each subject included in the first data set at second time in the future ("time Y" in FIG. 1). A database of the system also comprises a defining a relationship between the characteristic measurement and each subject, such that each characteristic measurement is assigned to a single subject from which the measurement originated. A "microbial nucleic acid feature" is defined above in section I(A).

Each subject included in the database is of the same species. Each subject may or may not be of the same breed or variety. In some embodiments, each subject included in a first data set is of the same breed or variety. In other embodiments, the plurality of subjects included in a first data set comprises two or more breeds or varieties. In each of the above embodiments, the plurality of subjects may or may not differ from each other in terms of a variety of factors including, but not limited to, age, provenance (i.e. source of the subject, which may refer to the mother, the location of birth, and/or the location growth of prior to weaning), distribution site (e.g. farm, city), physical location within distribution site (barn, pen, poultry house, tank, physical residence), diet and other environmental factors. In some embodiments, the subject may be human. Without wishing to be bound by theory, Applicants contemplate one or more databases may be used by a single animal growing operation that raises a species of animal at one or more locations. Multiple databases may be needed depending upon geographical and/or environmental differences that significantly affect the taxonomic features of an animal's gut microbiota within or between locations and/or the number and types of breed and varieties raised within or between each location, as well as differences in animal husbandry practices within or between locations.

(i) First Data Set

A first data set comprises a plurality of microbial nucleic acid features for each of a plurality of subjects. A microbial nucleic acid feature in a first data set is assigned a label or identifier, which is the anonymized or non-anonymized identity of the subject. Thus, a first data set includes, at a minimum, a relationship between an individual subject and the presence or absence (e.g. diversity) of the subject's gut microbiota as defined by a plurality of its microbial nucleic acid features, for a plurality of subjects. Preferably, a first data set of the present technology also includes a relationship between an individual subject and the abundance of the identified microbial nucleic acid features. When a microbial nucleic acid feature includes microbial taxonomic information, a first data set also includes a relationship between an individual subject and the presence, absence, or abundance of the subject's gut microbiota defined at one or more taxonomic levels, for a plurality of subjects. When a microbial nucleic acid features includes microbial functional information, a first data set also includes a relationship between an individual subject and the presence, absence or abundance of the subject's gut microbiota defined by one or more functional groups, for a plurality of subjects. When a microbial nucleic acid features includes microbial taxonomic and functional information, a first data set includes a relationship between an individual subject and the presence, absence or abundance of the subject's gut microbiota defined at one or more taxonomic levels and by one or more functional groups, for a plurality of subjects.

The gut microbiota, as defined by its microbial nucleic acid features, is known to vary in its composition between subjects (e.g. inter-subject variation). For example, between two subjects there may be variation in the presence of a microbial taxon defined at the phylum, class, order, family, genus, species, and/or strain level. Stated another way, one subject's gut microbiota may comprise a particular taxon of microorganism while a second subject's gut microbiota may lack that taxon. Variation may be found at a single taxonomic level or at multiple taxonomic levels. As a second example, between two subjects there may be variation in the abundance of a microbial taxon defined at the phylum, class, order, family, genus, species, or strain level. Stated another way, a particular taxon of microorganism may be present in two subjects, though the abundance of the taxon may be 100-fold greater in a first subject compared to a second subject. As another example, between two subjects there may be variation in the presence and/or abundance of nucleic acid products. Similar variation exists at the functional level. The magnitude of difference can and will vary between subjects.

The variance may be more than about 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1% between subjects. Alternatively, the variance may be more than about 50, 49, 48, 47, 46, 45, 44, 43, 42, 41, 40, 39, 38, 37, 36, 35, 34, 33, 32, 31, 30, 29, 28, 27, 26, 25, 24, 23, 22, or 21% between subjects. The variance may also be more than about 70, 69, 68, 67, 66, 65, 64, 63, 62, 61, 60, 59, 58, 57, 56, 55, 54, 53, 52, 51, 50, 49, 48, 47, 46, 45, 44, 43, 42, or 41% between subjects. The variance may also be more than about 90, 89, 88, 87, 86, 85, 84, 83, 82, 81, 80, 79, 78, 77, 76, 75, 74, 73, 72, 71, 70, 69, 68, 67, 66, 65, 64, 63, 62, or 61% between subjects. The variance may also be more than about 100, 99, 98, 97, 96, 95, 94, 93, 92, 91, 90, 89, 88, 87, 86, 85, 84, 83, 82, 81, 80, 79, 78, 77, 76, 75, 74, 73, 72, or 71% between subjects. The variance may be at least 2, at least 3, at least 4, at least 5, at least 6, at least 7, at least 8, at least 9, or at least 10-fold between subjects. Alternatively, the variance may be at least 10, at least 50, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000-fold or more between subjects. Thus, a first data set of the present technology includes a relationship between an individual subject and the composition of the subject's gut microbiota as defined by one or more microbial nucleic acid features, where there is inter-subject variation in the microbial nucleic acid features. More specifically, a first data set of the present technology may include a relationship between an individual subject and the composition of the subject's gut microbiota defined at one or more taxonomic levels, for a plurality of subjects, where there is inter-subject variation in the microbial taxonomic information. Alternatively, a first data set of the present technology may include a relationship between an individual subject and the composition of the subject's gut microbiota defined by one or more functional groups, for a plurality of subjects, where there is inter-subject variation in the microbial functional information.

A subject's gut microbiota, as defined by its microbial nucleic acid features, changes over time. Preferably, then, a first data set comprises microbial nucleic acid features for a plurality of subjects of approximately the same age. In some embodiments, a first data set comprises microbial nucleic acid features for a plurality of subjects that are approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days of age. In other embodiments, a first data set comprises microbial nucleic acid features for a plurality of subjects that are approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 385, 39, 40, 41, 42, 43, 44, 45, 46, 47, 48, 49, 50, 51, 52, or more weeks of age. In still other embodiments, a first data set comprises microbial nucleic acid features for a plurality of subjects that are less than about 1, 2, 3, 4, 5, 6, 7, 8, 9, or 10 weeks of age. In yet other embodiments, a first data set comprises microbial nucleic acid features for a plurality of subjects that are less than about 1, 2, 3, 4, 5, 6, 7, 8, 9, or 10 years of age. In some embodiments, the first data set comprises data from animals of mixed ages.

A subject's gut microbiota, as defined by its microbial nucleic acid features, may also significantly change in response to an event including, but not limited to, weaning, a change in diet, a change in geography, a change in housing, medical treatment, disease, reproductive maturity, or pregnancy. Generally, a first data set comprises microbial nucleic acid features for a plurality of subjects at a point in time before an event that significantly changes the gut microbiota and a second data set comprises a characteristic measurement for each subject at a point in time after the event occurs. Aspects of the second data set are described in further detail in Section I(C). A 'significant change in the gut microbiota' is defined as change in the overall community configuration of the microbiota such that an individual subject no longer clusters with its prior grouping.

The number of subjects included in the first data set can vary from database to database and system to system, and will depend upon the number of subjects needed to give the predictive model produced by the system an acceptable degree of statistical significance. Without wishing to be bound by theory, a greater number of individuals may be needed as genetic heterogeneity between subjects increases. Other factors that may influence the number of subjects needed to give a predictive model an acceptable degree of statistical significance are known to one skilled in the art. Non-limiting examples may include, gender, family structure of the subject (e.g. littermates, geographic groups, etc.). In some embodiments, the number of subjects included in the first data set may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more. In other embodiments, the number of subjects included in the first data set may be 50, 100, 150, 200, 250, 300, 350, 400, 450, 500, 550, 600, 650, 700, 750, 800, 850, 900, 950, 1000, or more.

In certain embodiments, subjects are swine. The gut microbiota of swine as defined by its microbial nucleic acid features may significantly change over time and/or in response to an event including, but not limited to, weaning, a change in diet, a change in geography, a change in housing, medical treatment, reproductive maturity, or pregnancy. Swine may be weaned at about 2 to about 4 weeks of age, or when they weigh about 5 to about 20 pounds. At this time they may be moved to a new location, such as a nursery, a grower building, or a wean-finish building. Swine moved to a nursery will be eventually moved to another location for the grow-finish phase. This may occur at about 4-6 weeks of age. The new location may or may not be at the same farm. During the grow-finish phase, swine may be fed one or more diets, may be vaccinated, may be administered antibiotics, may be housed in one or more enclosures in the same building, may be housed in one more enclosures in different buildings, may be housed in one or more enclosures on different farms, or a combination thereof. When swine reach a desired finishing weight they are typically brought to market. The finishing weight and age at which a finishing weight is achieved will vary depending upon the breed. Generally, finishing weight of swine may be about 200 pounds to about 350 pounds Animals may reach finishing weight at about 20 to about 30 weeks of age. Reproductive maturity will vary depending upon the breed. In some embodiments, a first data set comprises gut microbial taxonomic information for a plurality of subjects of approximately the same age, wherein the subjects are swine and the approximate age is selected from the group consisting of about 1 to about 5 days of age, about 5 to about 10 days of age, about 1 to about 2 weeks of age, about 1 to about 4 weeks of age, about 2 to about 4 weeks of age, about 3 to about 5 weeks of age, about 2 to about 6 weeks of age, about 4 to about 8 weeks of age, about 4 to about 6 weeks of age, about 6 to about 8 weeks of age, about 7 to about 10 weeks of age, about 8 to about 11 weeks of age, about 9 to about 12 weeks of age, about 6 to about 12 weeks of age, and about 8 to about 12 weeks of age. In other embodiments, a first data set comprises gut microbial taxonomic information for a plurality of subjects of approximately the same age, wherein the subjects are swine and the approximate age is selected from the group consisting of less than about 3 weeks of age, less than about 4 weeks of age, less than about 5 weeks of age, or less than about 6 weeks of age.

In certain embodiments, subjects are poultry. The gut microbiota of poultry may significantly change over time and/or in response to an event including, but not limited to, a change in diet, a change in geography, a change in housing, medical treatment, or reproductive maturity. Over a life cycle, poultry may be raised in one, two, three, four or more facilities (e.g. hatchery, brooder facility, intermediate facility, grow-out facility). Hatchlings are transferred from the hatchery over a period ranging from a few hours to one day. The new location may or may not be at the same farm. During the grow-out phase, poultry may be fed one or more diets, may be vaccinated, may be administered antibiotics, may be housed in one or more enclosures in the same building, may be housed in one or more enclosures in different buildings, may be housed in one or more enclosures on different farms, or a combination thereof. Diets may vary depending upon the age of the animal (e.g. starter feed vs. grower feed) and/or its intended utility (broiler vs. layer). When poultry raised for meat reach a desired finishing weight they are typically processed. The finishing weight and age at which a finishing weight is achieved will vary depending upon the breed, nutrition, and the market they are meant to fill. As a non-limiting example, female turkeys may be processed at about 6 to about 15 weeks of age or at a weight of about 8 to about 15 pounds (live weight); male turkeys may be processed at about 15 to about 25 weeks of age or at weight of about 30 to about 45 pounds (live weight); chickens may be processed at about 4 to about 7 weeks or at about 3 to about 5 pounds (live weight); ducks may be processed at about 5 to about 8 weeks or at about 5 to about 10 pounds (live weight). For breeding or egg-laying flocks, birds that reach sexual maturity are moved to a laying house or similar facility that acts as a mating house. Reproductive maturity will vary depending upon the breed. Laying hens begin laying eggs at approximately 18 weeks of age.

In certain embodiments, subjects are cattle. The gut microbiota of cattle as defined by its microbial nucleic acid features may significantly change over time and/or in response to an event including, but not limited to, weaning, a change in diet, a change in geography, a change in housing, medical treatment, reproductive maturity, or pregnancy. Cattle may be weaned at about 6 to about 8 months of age or at about 500 to about 600 pounds (live weight). Bull calves may be castrated and fed until market weight or separated out for use in breeding programs. After weaning, calves may be fed on grassland during a growing phase until they weigh about 750 to about 800 lbs. (live weight), at which point they are called stocker cattle. Stocker calves may be placed in a confinement feedlot for approximately 90 to 120 days until they reach a suitable finishing weight (e.g. finishing phase). Alternatively, weaned calves may be placed directly into a confinement feedlot for growing and finishing. During growing and finishing, cattle may be fed one or more diets, may be vaccinated, may be administered antibiotics, may be housed in one or more enclosures on a farm, may be housed in one or more enclosures on different farms. When cattle reach a desired finishing weight they are typically brought to market. The finishing weight and age at which a finishing weight is achieved will vary depending upon the breed. Generally, finishing weight of cattle may be about 1000 pounds to about 1500 pounds. The age at which cattle reach their finishing weight will vary by breed. Reproductive maturity will vary depending upon the breed but may generally occur by about 15 months of age.

In certain embodiments, subjects are humans. The gut microbiota of humans as defined by its microbial nucleic acid features may significantly change over time and/or in response to an event including, but not limited to, weaning, a change in diet, a change in housing, medical treatment, reproductive maturity, or pregnancy.

In certain embodiments, subjects are fish. The microbiota of fish as defined by its microbial nucleic acid features may significantly change over time and/or in response to an event including, but not limited to, a change in diet, a change in housing, medical treatment, disease, reproductive maturity, or pregnancy. An exemplary embodiment is salmon wherein after hatching, small fish are fed high-quality diets in freshwater for 6 to 12 months. These fish are then transported from the hatchery to marine farms, where they typically reach 8-10 lbs after 14-22 months.

In the above embodiments wherein microbial nucleic acid features are determined by a sequencing-based approach, microbial nucleic acid features for each subject may be determined from at least 5,000, at least 6,000, at least 7,000, at least 8,000, at least 9,000, at least 10,000, at least 11,000, at least 12,000, at least 13,000, at least 14,000, at least 15,000, at least 16,000, at least 17,000, at least 18,000, at least 19,000, at least 20,000, at least 21,000, at least 22,000, at least 23,000, at least 24,000, at least 25,000, at least 26,000, at least 27,000, at least 28,000, at least 29,000, at least 30,000, at least 31,000, at least 32,000, at least 33,000, at least 34,000, at least 35,000, at least 36,000, at least 37,000, at least 38,000, at least 39,000, at least 40,000, at least 41,000, at least 42,000, at least 43,000, at least 44,000, at least 45,000, at least 46,000, at least 47,000, at least 48,000, at least 49,000, at least 50,000, at least 51,000, at least 52,000, at least 53,000, at least 54,000, at least 55,000, at least 56,000, at least 57,000, at least 58,000, at least 59,000, or at least 60,000 sequencing reads from each sample. In some embodiments, microbial nucleic acid features for each subject are determined from at least 10 sequencing reads from each sample. The number of sequencing reads used to determine microbial nucleic acid features can and will vary, and in part, may be determined by the abundance of discriminatory features. Increasing the number of sequencing reads improves the likelihood that a rare discriminatory feature will be detected. Discriminatory features are described in further detail in Section I(D).

In the above embodiments wherein microbial nucleic acid features are determined using a high-density microarray, microbial nucleic acid features for each subject may be determined using an array comprising least 50,000, at least 60,000, at least 70,000, at least 80,000, at least 90,000, at least 100,000, at least 110,000, at least 120,000, at least 130,000, at least 140,000, at least 150,000, at least 160,000, at least 170,000, at least 180,000, at least 190,000, at least 200,000, at least 210,000, at least 220,000, at least 230,000, at least 240,000, at least 250,000, at least 260,000, at least 270,000, at least 280,000, at least 290,000, at least 300,000, at least 310,000, at least 320,000, at least 330,000, at least 340,000, at least 350,000, at least 360,000, at least 370,000, at least 380,000, at least 390,000, at least 400,000, at least 410,000, at least 420,000, at least 430,000, at least 440,000, at least 450,000, at least 460,000, at least 470,000, at least 480,000, at least 490,000, at least 500,000, at least 510,000, at least 520,000, at least 530,000, at least 540,000, at least 550,000, at least 560,000, at least 570,000, at least 580,000, at least 590,000, or at least 600,000 probes. The number of probes per microarray used to determine microbial nucleic acid features can and will vary, and in part, may be determined by the abundance of discriminatory features. Increasing the number of probes per array improves the likelihood that a rare discriminatory feature will be detected. Discriminatory features are described in further detail in Section I(D).

The number of features (microbial taxa/OTUs) included in the first data set can vary from database to database and system to system, and will depend upon: the number of subjects included in the first data set, the average alpha diversity (number of distinct taxa/features) physically present within each subject, the level of sequencing effort applied to each sample/subject (greater sequencing effort/depth may allow for the detection of more sensitive taxa), and the degree of homogeneity/heterogeneity in microbial profiles across subjects. Generally, a first data set will have a large number of features when the number of subjects is high, the average alpha diversity is high, the sequencing effort applied to each subject is high, and the degree of inter-subject profile heterogeneity is high. The number of features in a first data set will typically range from 100's to 10,000's, but may comprise as few as 10 or as many as 100,000.

(ii) Second Data Set

According to the present technology, a second data set comprises a characteristic measurement for each subject included in the first data set at second time and a defining relationship between the characteristic measurement and each subject. The phrase "a defining a relationship between a characteristic measurement and each subject" indicates the two types of information are linked (i.e. the characteristic measurement and the identity of the subject) such that in the second data set each characteristic measurement is assigned to a single subject from which the measurement originated.

A "characteristic", as used herein, refers to any measurable aspect of a subject's performance and health at a point in time after the collection of the fecal sample from which the first data set was produced (i.e. "a future time", or as depicted in FIG. 1 "time Y">"time X"). Measurement of a characteristic may be qualitative, semi-quantitative or quantitative. Non-limiting examples of a measurable aspect of a subject's performance and health include growth and body composition characteristics; digestive, nutritional, and metabolic characteristics; susceptibility to one or more diseases and the manifestations of a disease; immune characteristics; and reproductive characteristics. Suitable measurements of growth and body composition characteristics include, but are not limited to, measurements of height, weight, length, girth, lean body mass, average daily gain (ADG) in height, ADG in weight, ADG in length, ADG in girth, finishing weight, carcass weight, carcass muscling, carcass cutability, pattern of fat deposition, and meat quality. Suitable measurements of digestive, nutritional, and metabolic characteristics include, but are not limited to, measurements of feed conversion ratio, feed efficiency, nutrient utilization from feed, blood glucose concentration, blood triglyceride concentration, and serum IGF-1 concentration. Suitable measurements of susceptibility to one or more diseases and/or the manifestations of a disease include, but are not limited to, measurements of disease duration, disease severity, disease frequency, morbidity, mortality, resistance to disease (e.g. to enteropathogen infection), susceptibility to disease including but not limited to infectious diseases, pathogen carriage, and pathogen shedding. Suitable measurements of immune characteristics include measurements of response to vaccination, pathogen specific antibody count, and gut inflammation. Suitable measurements of reproductive characteristics include, but are not limited to, measurements of litter size, frequency of still born births, and average litter birth weight. Methods to measure the above characteristics are well known to one skilled in the art of animal husbandry, veterinary practice or medicine.

As noted above in Section I(B), a subject's gut microbiota as defined its microbial nucleic acid features may significantly change in response to an event. A characteristic measurement may occur after an event that significantly changes the gut microbiota, an amount of time after the fecal sample used to produce the first data set was collected, or at the time of particular even in the subject's life (e.g. slaughter, birth, weaning, etc.). A characteristic measurement may occur at least 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, at least 730 or more days after the fecal sample used to produce the first data set was collected. The future time may change between species, breeds or varieties, as well as between future characteristics. Using finishing weight of swine as a non-limiting example of a characteristic measurement, a fecal sample may be obtained at about 2 to about 6 weeks of age, about 4 to about 8 weeks of age, about 6 to about 10 weeks of age, about 8 to about 12 weeks of age, about 10 to about 14 weeks of age, about 12 to about 16 weeks of age, or about 14 to about 18 weeks of age and finishing weight may be measured at about 20 to about 30 weeks. Using finishing weight of poultry as a second non-limiting example of a characteristic measurement, and a fecal sample may be obtained at about 1 to about 7 days of age, about 4 to about 11 days of age, about 7 to about 14 days of age, about 10 to about 17 days of age, about 14 to about 21 days of age, about 17 to about 24 days of age and finishing weight measured at about 4 to about 7 weeks.

In some embodiments, a subject is a swine and a characteristic measurement is a measurement of one or more performance and health include growth and body composition characteristics; one or more digestive, nutritional, and metabolic characteristics; one or more susceptibility to one or more diseases and the manifestations of a disease; one or more immune characteristics; and reproductive characteristics. In other embodiments, a subject is a swine and a characteristic measurement is a measurement of one or more height, weight, length, girth, lean body mass, average daily gain (ADG) in height, ADG in weight, ADG in length, ADG in girth, finishing weight, carcass weight, carcass muscling, carcass cutability, pattern of fat deposition, and meat quality. In other embodiments, a subject is a swine and a characteristic measurement is a measurement of one or more of feed conversion ratio, feed efficiency, nutrient utilization from feed, blood glucose concentration, blood triglyceride concentration, and serum IGF-1 concentration. In other embodiments, a subject is a swine and a characteristic measurement is a measurement of one or more of disease duration, disease severity, disease frequency, morbidity, mortality, resistance to disease (e.g. to enteropathogen infection), susceptibility to disease including but not limited to infectious diseases, pathogen carriage, and pathogen shedding. In other embodiments, a subject is a swine and a characteristic measurement is a measurement of one or more of response to vaccination, pathogen specific antibody count, and gut inflammation. Suitable measurements of reproductive characteristics include, but are not limited to, measurements of litter size, frequency of still born births, and average litter birth weight. Methods to measure the above characteristics are well known to one skilled in the art of animal husbandry, veterinary practice or medicine. In alternative embodiments, a subject is selected from the group consisting of poultry, cats, dogs, horses, humans, non-human primates, rabbits, rodents, cattle, sheep, goats, llama, alpacas, fish, or any other subject defined herein.

In some embodiments, measured characteristics of the second data base relate to the performance of the offspring of the subjects for whom nucleic acid features are determined. In some embodiments, a characteristic measurement is a measurement of one or more of performance and health including growth and body composition characteristics of the offspring; one or more digestive, nutritional, and metabolic characteristics of the offspring; susceptibility to one or more diseases and the manifestations of a disease in the offspring; one or more immune characteristics of the offspring; or one or more reproductive characteristics of the offspring. In other embodiments, a characteristic measurement is a measurement of one or more of height, weight, length, girth, lean body mass, average daily gain (ADG) in height, ADG in weight, ADG in length, ADG in girth, finishing weight, carcass weight, carcass muscling, carcass cutability, pattern of fat deposition, and meat quality of the offspring. In other embodiments, a characteristic measurement is a measurement of one or more of feed conversion ratio, feed efficiency, nutrient utilization from feed, blood glucose concentration, blood triglyceride concentration, and serum IGF-1 concentration of the offspring. In other embodiments, a characteristic measurement is a measurement of one or more of disease duration, disease severity, disease frequency, morbidity, mortality, resistance to disease (e.g. to enteropathogen infection), susceptibility to disease including but not limited to infectious diseases, pathogen carriage, and pathogen shedding of the offspring. In other embodiments, a characteristic measurement is a measurement of one or more of response to vaccination, pathogen specific antibody count, and gut inflammation in the offspring. Suitable measurements of reproductive characteristics include, but are not limited to, measurements of litter size, frequency of still born births, and average litter birth weight. Methods to measure the above characteristics are well known to one skilled in the art of animal husbandry, veterinary practice or medicine. In some embodiments, the subject is a swine. In alternative embodiments, a subject is selected from the group consisting of poultry, cats, dogs, horses, humans, non-human primates, rabbits, rodents, cattle, sheep, goats, llama, alpacas, fish, or any other subject defined herein.

(iii) Additional Data Sets

When a database of the system comprises more than a first and a second data set, each additional data set may comprise an additional characteristic measurement for each subject included in the first data set. An additional characteristic measurement may be the same or different than the characteristic(s) comprising the second data set and may be measured at any time before, during and/or after the collection of the fecal sample from which the first data set was produced. Each additional data set will be otherwise as described for a second data set.

In certain embodiments, a first data set may be used with one or more additional data sets to improve the model. In these embodiments, while the primary feature type will be that of microbial nucleic acid, other feature types can be incorporated into the model-building process to improve the predictive model's performance. The "other feature types" may be one more additional characteristics present in an additional data set. Non-limiting examples of suitable characteristics may include weaning weight, health status and other characteristics as defined above in Section I(B)(ii).

C. At Least One Processor

Figure 10:
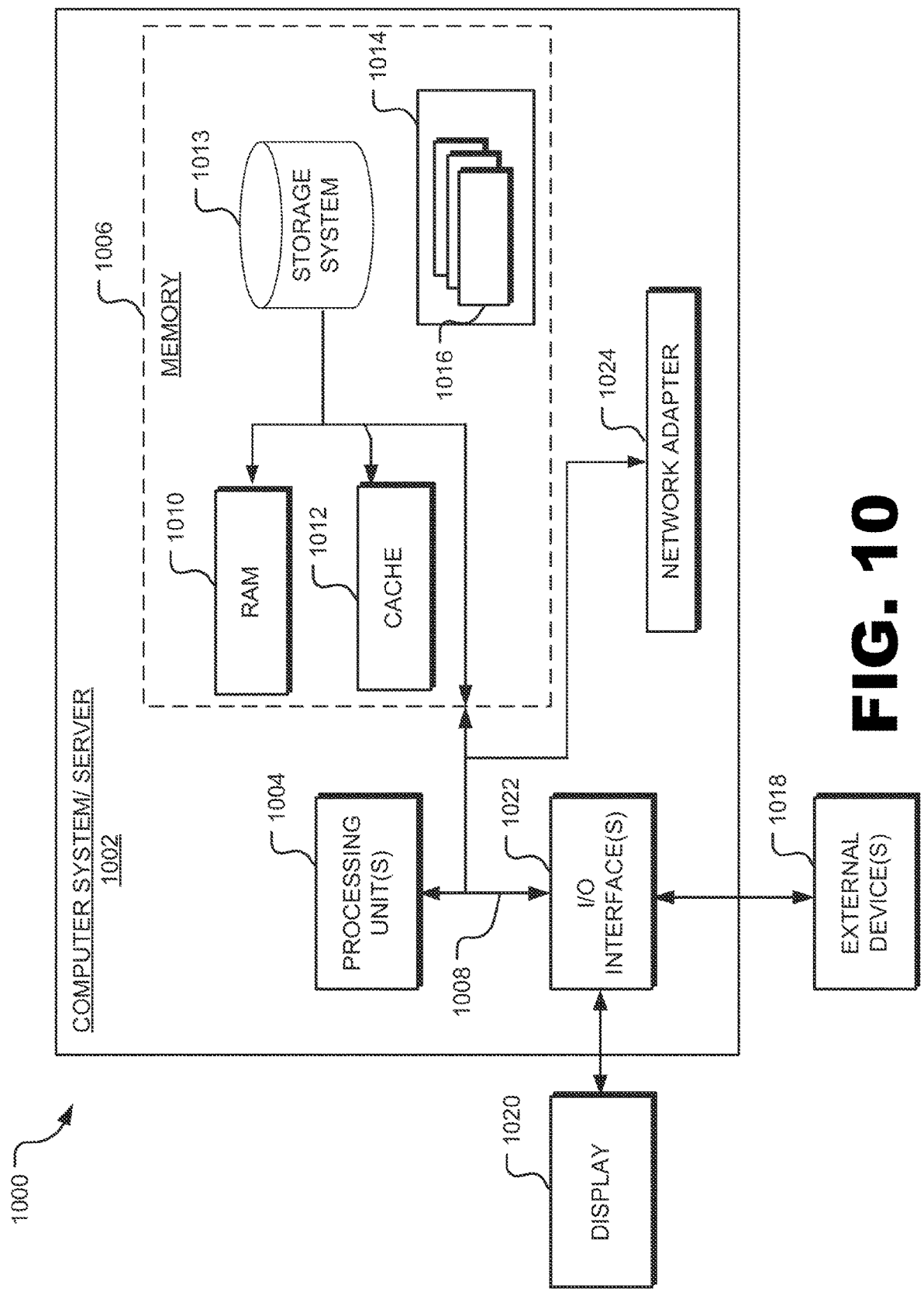
FIG. 10 provides an example computing architecture.

FIG. 10 illustrates an example computing node 1000, which may comprise an implementation of the server 802, 902, and/or the sequencers 804, 806, and 808. The computing node 1000 represents only one example of a suitable computing device and is not intended to suggest any limitation as to the scope of use or functionality of embodiments of the present technology described herein. Regardless, the computing node 1000 is capable of being implemented and/or performing any of the functionality set forth hereinabove, or below, such as for example, executing a learning application, as will be described in more detail below.

The computer node 1000 may include a computer system/server 1002, which is operational with numerous other general purpose or special purpose computing system environments or configurations. Examples of well-known computing systems, environments, and/or configurations that may be suitable for use with computer system/server 1002 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 1002 may be described in the general context of computer system executable instructions, such as program modules, being executed by a computer system. Generally, program modules may include routines, programs, objects, components, logic, data structures, and so on that perform particular tasks or implement particular abstract data types. Computer system/server 1002 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 1002 in computing node 800 is shown in the form of a general-purpose computing device. The components of computer system/server 1002 may include, but are not limited to, one or more processors or processing units 1004, a system memory 1006, and a bus 1008 that couples various system components including system memory 1006 to processor 1004.

Bus 1008 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 1002 typically includes a variety of computer system readable media. Such media may be any available media that is accessible by computer system/server 1002, and it includes both volatile and non-volatile media, removable and non-removable media.

System memory 1006 can include computer system readable media in the form of volatile memory, such as random access memory (RAM) 1010 and/or cache memory 1012. Computer system/server 1002 may further include other removable/non-removable, volatile/non-volatile computer system storage media. By way of example only, storage system 1013 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1008 by one or more data media interfaces. As will be further depicted and described below, memory 1006 may include at least one program product having a set (e.g., at least one) of program modules that are configured to carry out the functions of embodiments of the present technology.

Program/utility 1014, having a set (at least one) of program modules 816, may be stored in memory 1006 by way of example, and not limitation, as well as an operating system, one or more application programs, other program modules, and program data. Each of the operating system, one or more application programs, other program modules, and program data or some combination thereof, may include an implementation of a networking environment. Program modules 1016 generally carry out the functions and/or methodologies of embodiments of the present technology as described herein.

Computer system/server 1002 may also communicate with one or more external devices 1018 such as a keyboard, a pointing device, a display 1020, etc.; one or more devices that enable a user to interact with computer system/server 1002; and/or any devices (e.g., network card, modem, etc.) that enable computer system/server 1002 to communicate with one or more other computing devices. Such communication can occur via Input/Output (I/O) interfaces 1022. Still yet, computer system/server 1002 can communicate with one or more networks such as a local area network (LAN), a general wide area network (WAN), and/or a public network (e.g., the Internet) via network adapter 1024. As depicted, network adapter 1024 communicates with the other components of computer system/server 1002 via bus 1008. It should be understood that although not shown, other hardware and/or software components could be used in conjunction with computer system/server 1002. Examples, include, but are not limited to: microcode, device drivers, redundant processing units, external disk drive arrays, RAID systems, tape drives, and data archival storage systems, etc.

D. Learning Application

In another aspect, a system comprises a program/utility executed by a processor that is a learning application. A learning application comprises instructions to process the first data set and the second data set to identify inter-subject variation in the microbial nucleic acid features of the first data set that relate to inter-subject variation in the characteristic measurements in the second data, and identify microbial nucleic acid features that discriminate a characteristic. A microbial nucleic acid feature that differentiates a characteristic refers to a feature whose inclusion in the algorithm training/model-building process minimizes the prediction error of the resulting model most effectively. Stated another way, a microbial nucleic acid feature that discriminates a characteristic refers to a feature whose exclusion from the algorithm training/model-building process leads to a meaningful increase in prediction error. In preferred embodiments, a learning application produces a feature importance score. Feature importance scores are a by-product of the learning application's main focus, which is to construct a model capable of predicting some output value (from the second data set) based on an ensemble of input values in the first data set. Feature importance scores may be used to inform the selection of microbial nucleic acid features when a sparse model is desired. The distribution of feature importance scores may include negative to positive values, or may include only positive values. In certain embodiments, features with high predictive power may exist in the right (positive) tail of this distribution.

A learning application may be an unsupervised learning algorithm or, more preferably a supervised learning algorithm. Without wishing to be bound by theory, unsupervised methods may be helpful in data mining, especially for identifying important features, while supervised methods may be used to build predictive models and create generalized functions that can be applied to other data sets. Non-limiting examples of unsupervised methods include approaches like PCA/PCoA, hierarchical clustering, and hidden Markov models (HMMs). A skilled artisan will appreciate that the art provides multiple techniques to identify information from a first data set that positively or negatively correlates with information in a second data set in order to create a predictive model. Suitable learning algorithms are known in the art and may include, but are not limited to, random forests, nearest shrunken centroids, the elastic net, and support vector machines.

A learning application of the present technology may receive all the information in the first and second data set, or may receive only a portion of the data comprising the first data set and all the information comprising the second data set. As a non-limiting example, a first data set may comprise gut microbial taxonomic information from a fecal nucleic acid sample, wherein the gut microbial taxonomic information comprises nucleic acid sequences assigned to operational taxonomic units (OTUs). A learning application may receive each OTU assigned from the sample or only a subset of OTUs assigned from the sample. A skilled artisan may exclude one or more OTUs from a first data set to produce a subset if an OTU is too sparse or rare to be considered reliable, or for any other reason that reduces confidence in the reliability of an OTU, including having a negative feature score. Though exemplified using nucleic acid sequences assigned to OTUs, this approach of selecting a reliable subset of microbial nucleic acid features from a first data set to use as an input for a learning application is applicable to all microbial nucleic acid features described herein.

In some embodiments, a learning application of the present technology functions to identify a plurality of continuous variables from a first data set (i.e. a plurality of microbial nucleic acid features) that positively or negatively correlates with a continuous or qualitative/categorical variable in a second data set (i.e. a characteristic measurement). As used herein, this is referred to as "feature selection". In certain embodiments, feature selection may be used to pick the 'best' features to include in a sparse model.

In other embodiments, a learning application of the present technology may use all the features in an input data set to make a prediction about some output variable, without performing feature selection. In our case, we filter down to a handful of features (ignoring the vast majority of information in the input data) because many features are 'noisy' and provide no predictive value for our model, or worse, actually hurt the model's performance (i.e., have negative feature importance scores).

II. Methods of Using a System for Predicting a Future Characteristic

In another aspect, the present disclosure provides a method for predicting a characteristic in a subject. The method comprises (1) using a system to identify microbial nucleic acid features that positively discriminate a characteristic to be predicted, (2) selecting a set comprising a plurality of microbial nucleic acid features, wherein the set can be used to create a predictive model defining the relationship between the features of the set and the characteristic, (3) determining the microbial nucleic acid features in a subject, and (4) applying the predictive model to the subject's nucleic acid features to predict the characteristic. Suitable systems are described in detail in Section I. The subject of the prediction is the same species as the subjects comprising the database of the system. A prediction for a new subject may be made using all the microbial nucleic acid features comprising the first data set, or only those features included as parameters in the predictive model.

No single microbial nucleic acid feature is likely to be highly predictive of a characteristic on its own, because of inter-subject microbiome variability and functional redundancy between taxa. A useful predictive model, therefore, must incorporate a number of the most discriminatory microbial nucleic acid features. A suitable predictive model may incorporate at least three discriminatory microbial nucleic acid features. For example, a suitable predictive model may incorporate 3, 4, 5, 6, 7, 8, 9, 10, 11, 12, 13, 14, 15, 16, 17, 18, 19, 20 or more discriminatory microbial nucleic acid features. Alternatively, a suitable predictive model may incorporate at least 5, 10, 15 or 20 discriminatory microbial nucleic acid features, including about 3 to about 5, about 5 to about 10, about 10 to about 15, or about 10 to about 15 discriminatory microbial nucleic acid features. The number of features may be empirically chosen based on which number of features gives the best performance. Alternatively, the number of features may be determined by the feature importance score, whereby features included are those with a feature importance score greater than the absolute value of the 'worst' feature importance score in the distribution of all scores. The option described above would set a cutoff between the main distribution and these highly predictive features, where the cutoff is as far to the right of zero as the most negative feature importance score to the left of zero.

Generally speaking, selecting discriminatory features that impact model positive performance improves the predictive accuracy of the final model and produces a more interpretable model by reducing the number of features. Suitable methods are known in the art to select an appropriate set of discriminatory features and include, but are not limited to, filter methods, wrapper methods and embedded feature selection techniques. Filter methods are completely agnostic to the choice of learning algorithm being used, and typically use a two-step process. First, a univariate test (e.g. t-test) or multivariate test (e.g. a linear classifier built with each unique pair of features) is performed to estimate the relevance of each feature, and select (1) all features whose scores exceed a predetermined threshold or (2) the best n features for inclusion in the model; then run a classifier on the reduced feature set. The choice of n can be determined using a validation data set or cross-validation on the training set. A wrapper uses the classifier itself to evaluate subsets of features. This leads to a computationally intensive search: an ideal wrapper would retrain the classifier for all feature subsets, and choose the one with the lowest validation error. The search is, however, not tractable for high-dimensional data sets; hence, the wrapper must use heuristics during the search to find the optimal feature subset. The use of a heuristic limits the wrapper's ability to interact with the classifier for two reasons: the inherent lack of optimality of the search heuristic, and the compounded lack of optimality in cases where the wrapper's optimal feature set differs from that of the classifier. Embedded approaches to feature selection perform an integrated search over the joint space of model parameters and feature subsets so that feature selection becomes an integral part of the learning process. Alternatively, one skilled in the art may use a hybrid of the methods described above. In another alternative, a skilled artisan may use Random Forest regression analysis.

In certain embodiments, a method for predicting a characteristic in a subject may further comprise use of an additional data set, as described above. The method may comprise processing the first data set, the second data set and the one or more additional data sets to identify inter-subject variation in the nucleic acid features of the first data set and the one or more additional data sets that relate to inter-subject variation in the characteristic measurements in the second data set.

III. Methods of Using Future Characteristic Predictions

A system of the present technology may be used to generate a predictive model. Such a predictive model has several different uses that are also contemplated herein.

For instance, a predictive model may be used to predict a physical characteristic of a subject. In such methods, a microbiota sample collected from the subject may be used, in conjunction with the model, to predict a physical characteristic of the subject. Non-limiting examples of a physical characteristic may be height, weight, length, girth, lean body mass, average daily gain (ADG) in height, ADG in weight, ADG in length, ADG in girth, finishing weight, carcass weight, carcass muscling, carcass cutability, pattern of fat deposition, meat quality, or a combination thereof. Predictions may be used to make management decisions for individual animals that allow an increase in profit per animal.

For example, in one embodiment, the physical characteristic may be average daily weight gain. By way of non-limiting example, a microbiota sample may be collected from a livestock animal at the time of weaning, and used, in conjunction with the model detailed herein, to predict the average daily weight gain of the subject at the time of slaughter. This, therefore, allows management decisions to be made for individual animals. For example, interventions may be ordered for animals with low daily weight gain predictions, so as to increase daily weight gain and therefore increase profit per animal. Suitable, non-limiting examples of interventions may include different feed rations, different housing conditions, administration of different supplements and/or medications, administration of one or more vaccines, or a combination thereof.

In another embodiment, a digestive, nutritional, or metabolic characteristic may be predicted by a model of the present technology. These include, but are not limited to, measurements of feed conversion ratio, feed efficiency, nutrient utilization from feed, blood glucose concentration, blood triglyceride concentration, and serum IGF-1 concentration. Again, predictions may be used to make management decisions for individual animals that allow an increase in profit per animal.

For example, in one embodiment, the digestive, nutritional, or metabolic characteristic may be feed efficiency. By way of non-limiting example, a microbiota sample may be collected from a livestock animal, and used, in conjunction with the model detailed herein, to predict the feed efficiency of the subject at the time of slaughter. This, therefore, allows management decisions to be made for individual animals. For example, interventions may be ordered for animals with low feed efficiencies, so as to increase feed efficiency and therefore increase profit per animal. Suitable, non-limiting examples of interventions may include different feed rations, different housing conditions, administration of different supplements and/or medications, administration of one or more vaccines, or a combination thereof.

In yet another embodiment, a predictive model may be used to identify subjects at risk for a particular disease or disorder. In such methods, a microbiota sample collected from the subject may be used, in conjunction with the model, to predict which subjects are more susceptible to a particular disease or disorder. Alternatively, a microbiota sample collected from the subject may be used, in conjunction with the model, to predict an immune characteristic of the subject that impacts susceptibility to a disease or disorder. "Susceptibility," as used herein, may be measured in terms of disease duration, disease severity, disease frequency, morbidity, mortality, resistance to disease (e.g. to enteropathogen infection), pathogen carriage, and pathogen shedding. Suitable measurements of immune characteristics include measurements of response to vaccination, pathogen specific antibody count, and gut inflammation. Similar to methods described above, the predictions generated by the model allow for management decisions to be made for individual animals. For example, interventions may be ordered for susceptible animals to reduce incidence of disease or disorders, and therefore, to increase profit per animal. Suitable non-limiting examples of interventions may include different feed rations, different housing conditions, administration of different supplements and/or medications, administration of one or more vaccines, or a combination thereof.

In some embodiments, the predictive model relates to performance of the offspring of the subjects for whom nucleic acid features are determined. In some embodiments, offspring performance relates to growth and body composition characteristics of the offspring; one or more digestive, nutritional, and metabolic characteristics of the offspring; susceptibility to one or more diseases and the manifestations of a disease in the offspring; one or more immune characteristics of the offspring; or one or more reproductive characteristics of the offspring. In other embodiments, offspring performance relates to one or more of height, weight, length, girth, lean body mass, average daily gain (ADG) in height, ADG in weight, ADG in length, ADG in girth, finishing weight, carcass weight, carcass muscling, carcass cutability, pattern of fat deposition, and meat quality of the offspring. In other embodiments, offspring performance relates to one or more of feed conversion ratio, feed efficiency, nutrient utilization from feed, blood glucose concentration, blood triglyceride concentration, and serum IGF-1 concentration of the offspring. In other embodiments, offspring performance relates to one or more of disease duration, disease severity, disease frequency, morbidity, mortality, resistance to disease (e.g. to enteropathogen infection), susceptibility to disease including but not limited to infectious diseases, pathogen carriage, and pathogen shedding of the offspring. In other embodiments, offspring performance relates to one or more of response to vaccination, pathogen specific antibody count, and gut inflammation in the offspring. Suitable measurements of reproductive characteristics include, but are not limited to, measurements of litter size, frequency of still born births, and average litter birth weight. Methods to measure the above characteristics are well known to one skilled in the art of animal husbandry, veterinary practice or medicine. In some embodiments, the subject is a swine. In alternative embodiments, a subject is selected from the group consisting of poultry, cats, dogs, horses, humans, non-human primates, rabbits, rodents, cattle, sheep, goats, llama, alpacas, fish, or any other subject defined herein.

Alternatively, a predictive model of the present technology may be used to identify subjects for use in a breeding program. In such methods, a microbiota sample collected from the subject may be used, in conjunction with the model, to predict a reproductive characteristic of the subject. Non-limiting examples of reproductive characteristics may include but are not limited to, measurements of litter size, frequency of still born births, and average litter birth weight. Predictions may be used to make management decisions for individual animals that allow an increase in profit per animal. For example, a subject predicted to have a low litter size, or a high frequency of still borns, may not be chosen for a breeding program. Or, additional interventions may be appropriate for certain individuals. Suitable interventions may include, but are not limited to, different feed rations, different housing conditions, administration of different supplements and/or medications, administration of one or more vaccines, or a combination thereof.

In a particular embodiment, a predictive model of the present technology may be used to identify a subject for use in a breeding program (e.g., as in a breeding index or method to calculate an estimated breeding value for a given animal) based on the subject's heritability of a trait. As used herein, "heritability of a trait" refers to the ability of the subject to pass a defined trait to offspring. In certain embodiments, a method for identifying a subject for use in a breeding program may comprise (1) an analysis of the subject's microbiota, in conjunction with a model described herein, to predict the heritability of a trait for a subject, and (2) an analysis of the subject's genome.

DEFINITIONS

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, "average daily gain" refers to the amount of weight gained per day for a subject over a given period of time.

As used herein, "feed conversion ratio" refers to a measure of a subject's efficiency in converting feed mass into increases of a desired output and is calculated by dividing the mass of the food eaten by the output for a specified period. For example, if an animal is raised for meat (e.g. swine, poultry, fish), the output may be the mass gained by the animal. If an animal is raised for another intended purpose, the output will be different. The term "feed conversion ratio" may be used interchangeably with the terms "feed conversion rate" or "feed conversion efficiency".

As used herein, "finishing weight" or "finished market weight" refers to the live weight of a production animal taken immediately before slaughter.

As used herein, "characteristic" refers to any measurable aspect of a subject's performance and health at a point in time after the collection of the fecal sample from which the first data set was produced (i.e. "a future time").

As used herein, "microbial nucleic acid feature" refers to a measurement of the amount of a nucleic acid in a nucleic acid sample that is either qualitative (present/absent) or quantitative (abundance of a nucleic acid). Microbial nucleic acid feature also refers to microbial functional information and microbial taxonomic information.

As used herein, "microbial functional information" refers to a nucleic acid assigned a functional classification in a nucleic acid sample.

As used herein, "microbial taxonomic information" refers to a nucleic acid assigned a taxonomic classification in a nucleic acid sample.

As used herein, "nucleic acid" refers to DNA, RNA, or DNA from amplified product. Included in the definition is chromosomal DNA, mRNA, tRNA, rRNA, and cDNA.

As used herein, "nucleic acid sample" refers to a plurality of heterogeneous nucleic acids produced by a subject's gut microbiota.

As used herein, "OTU" refers to an operational definition of a taxonomic level or an "operational taxonomic unit". Nucleic acid sequences are generally collapsed into OTUs based on sequence similarity thresholds for downstream analyses. The threshold is used as a proxy for divergence at that taxonomic unit. For example, a threshold of 97% may be used as a threshold for species-level divergence.

As used herein, "production animal" refers to an animal that produces food or other consumer product for humans.

As used herein, "weaning" refers to the process of gradually taking food otherwise than by nursing or by a bottled substitute. In humans, weaning may correspond to the transition from liquid to solid foods. Weaning may be associated with a substantial change in the subject's gut microbiota.

EXAMPLES

The following examples illustrate various iterations of the present technology. However, those of skill in the art should, in light of the present disclosure, appreciate that many changes can be made in the specific embodiments which are disclosed and still obtain a like or similar result without departing from the spirit and scope of the present technology.

Example 1

Figure 2:
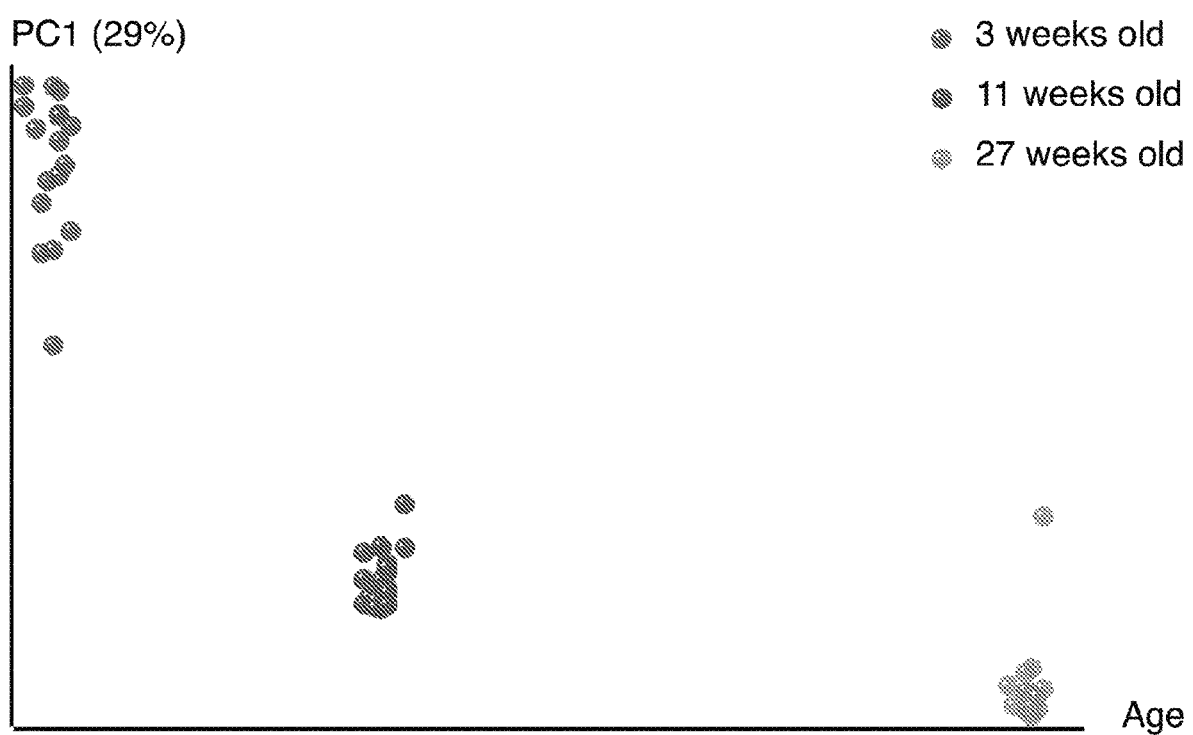
FIG. 2 graphically depicts the ordered development of the swine microbiota over time. Shown is the result of subjecting microbial community data (e.g., 16S amplicon sequencing data) to an ordination method known as principal coordinates analysis (PCoA). PCoA is a multivariate technique used to explore/visualize the similarities/dissimilarities between samples described in a distance matrix. PCoA maximizes the linear correlation between the values in the distance matrix (here, Hellinger distances) and the distance between the points within an ordination plot. In the two-dimensional plot provided, the age of each animal at the time of sample collection is graphed along the x-axis while the distance between communities (as judged by comparing sample values along the first principal coordinate, PC1) is shown along the y-axis. PC1 can be thought of the axis accounting for the greatest proportion of sample variance when the pairwise distances for all k samples are plotted in k−1 dimensional space. Two communities having small differences in their y-values can thus be thought of as being more similar than communities having large differences in their y-values. Each microbial community (i.e., sample) is depicted as a single point/orb in the plot. Each orb color corresponds to a different age group.
Figure 3:
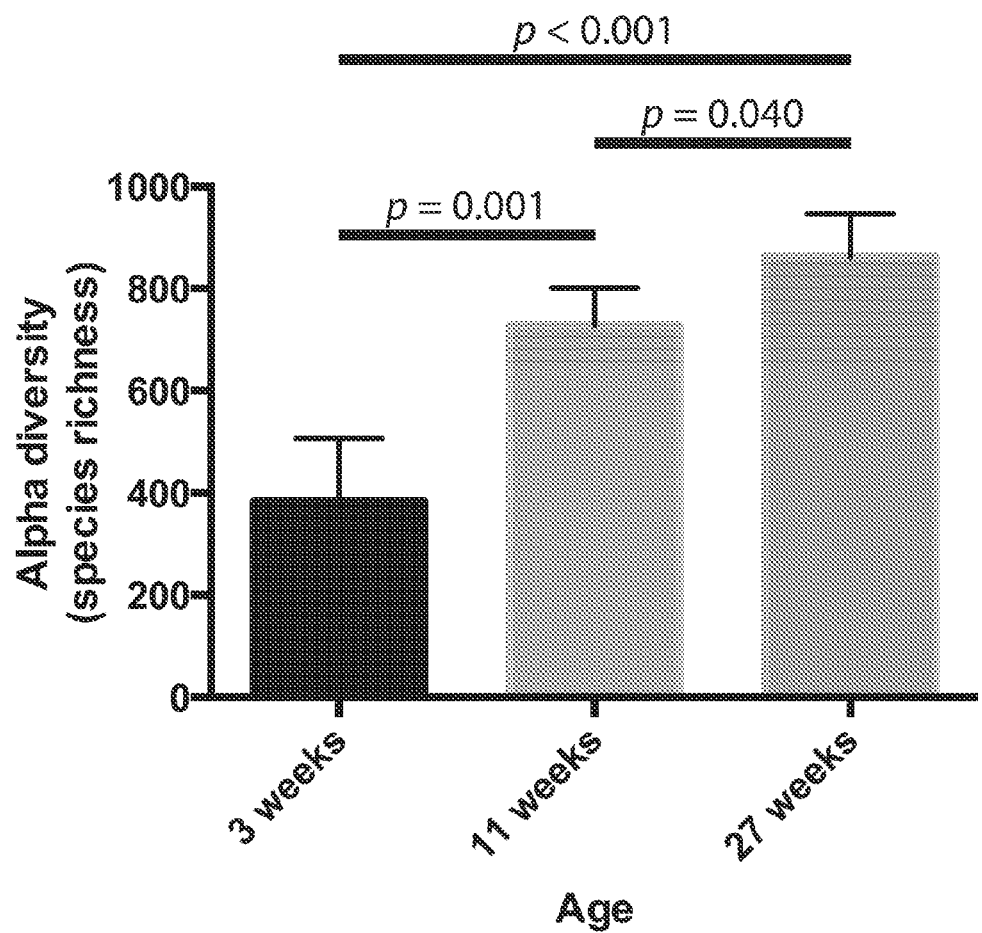
FIG. 3 depicts a graph showing the change in alpha diversity of the swine gut microbiota (y-axis) at 3, 11 and 27 weeks of age (x-axis). Statistical test performed: One-way ANOVA (nonparametric Kruskal-Wallis test, with Dunn's multiple comparison's test). p values shown are adjusted for multiple comparisons.

The Structure of a Subject's Microbiota is Subject to Orderly Developmental Change as a Subject Ages Fecal samples were obtained from a group of swine at 3 (n=16), 11 (n=15), and 27 (n=15) weeks of age and the gut microbiota characterized. The data for each timepoint were not from the same animals (i.e. the samples were collected contemporaneously from three different groups). As shown in FIG. 2, the structure of the swine microbiota develops over time. In this analysis, a matrix describing OTU abundances in each animal was used to calculate pairwise distances between samples using a Hellinger distance metric. Sample distances were then subjected to ordination by principle coordinates analysis (PCoA) to generate the plot shown in FIG. 2. This plot is the result of projecting the multi-dimensional distance information in the distance matrix onto a single axis, PC1, and plotting each sample's coordinate along PC1 against the age of the animal from which each sample was collected. When the dimensionality of microbiome data is reduced via ordination, communities are seen to evolve along a specific trajectory. The reorganization of the swine microbiota over time coincides with significant increase in community diversity (FIG. 3). Changes in the abundance of individual taxa drive these diversity increases and the developmental progression illustrated in FIG. 2. Temporal profiling of a single animal is expected to produce similar results.

Example 2

Classification Methods Distill Microbiota Data Down to Key Taxonomic Features

Figure 4:
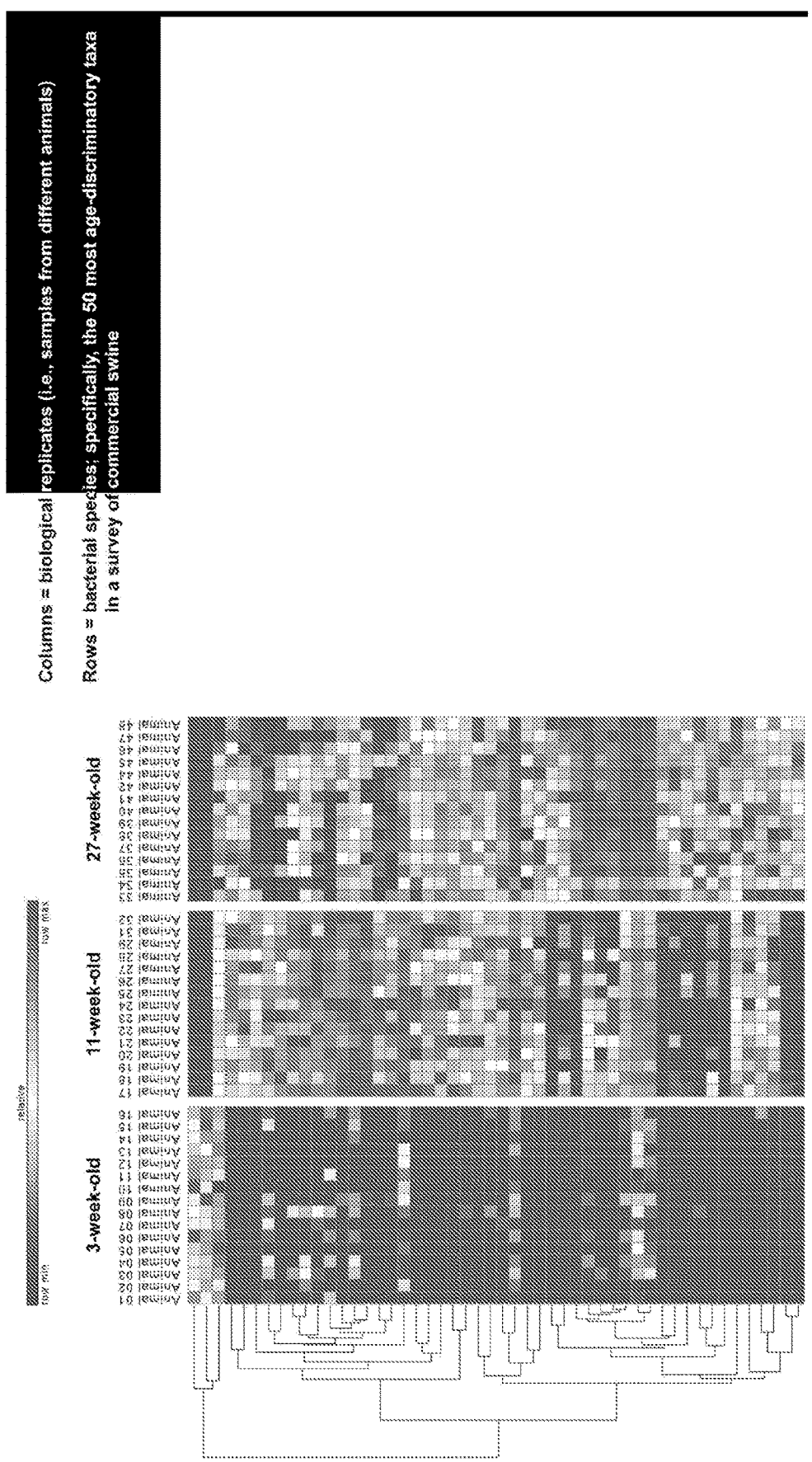
FIG. 4 illustrates in a table the relative abundance of the 50 most age-discriminatory taxa in a survey of commercial swine. By age-group, each column in the table represents a biological replicate (i.e. a different animal). Each row is a distinct OTU, defined here as about 97% nucleic acid sequence similarity. Note the inter-subject variation within each age group and between age groups. The dendogram to the left of the table illustrates the level of similarity between different OTU profiles across samples, based on hierarchical clustering.

Two types of information known for each sample included in the analysis in FIG. 2 were passed as training data to the Random Forest algorithm (run in classification mode): (i) the abundance of each operational taxonomic unit (OTU) identified in each sample, and (ii) the age of the animal from which each sample was collected. After sorting the importance scores for all features in the resulting predictive model, the top 50 features (i.e., those with the highest positive scores) were identified. Shown in FIG. 4 is a heat map illustration of the relative abundance for each of these top 50 features across 46 commercial swine, binned by their known age. In this representation, each row corresponds to a distinct OTU, and each column corresponds to a distinct subject (animal). All features have been subjected to simple hierarchical clustering to emphasize the relatedness between patterns in feature abundances across animals of different ages (feature relatedness can be assessed using the dendrogram to the left of the heat maps). Importantly, a sparse model comprising only the 50 age-discriminatory features shown performed sample age classification perfectly on out-of-bag data. This demonstrates that the system can be used with a high degree of success to identify features that successfully discriminate samples by an output variable of interest.

Example 3

Figure 5:
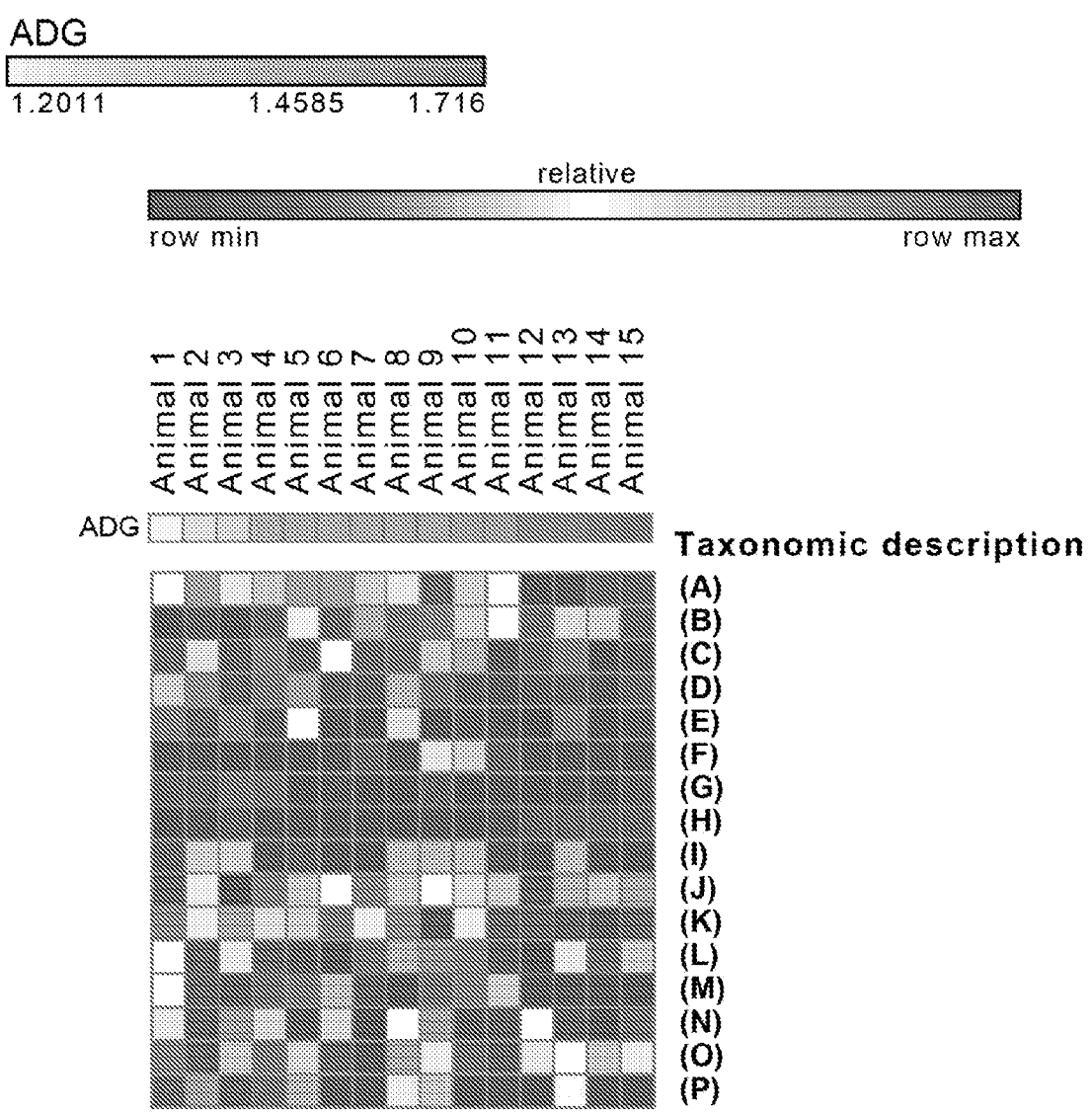
FIG. 5 illustrates the relative abundances of 16 OTUs comprising a sparse Random Forest model, based on 16S amplicon sequencing data from 11-week-old pigs. Each column represents a biological replicate, and columns have been sorted left-to-right in ascending order based on the average daily gain (ADG) of the animals (minimum=1.2011, maximum=1.716; see white-to-green color key for ADG). Each row labeled with a taxonomic description denotes an OTU from the model, while the color of each cell in a row signifies the abundance of that OTU in a sample relative to the minimum (blue) or maximum (red) observed for that OTU across all 15 samples.

Both Positively and Negatively Correlated Microbiota Features can be Incorporated into Growth Prediction Models Two types of information known for each sample from the 11-week-old cohort in the analysis in FIG. 2 were passed as training data to the Random Forest algorithm (run in regression mode): (i) the abundance of each operational taxonomic unit (OTU) identified in each sample, and (ii) the average daily gain (ADG) of the animal from which each sample was collected. Here, ADG was calculated as the difference between a weight measurement at approximately 27 weeks of age and farrowing (i.e., total weight gain since birth) divided by the age of the animal in days at the time of the later weight measurement. After sorting the importance scores for all features in the resulting predictive model, the top 16 features (i.e., those with the highest positive scores) were identified. FIG. 5 provides a heat map illustration of the relative abundance of each of these "ADG-discriminatory" OTUs in each of the subject animals at approximately 11 weeks of age. In this representation, each row corresponds to a distinct OTU, and each column corresponds to a distinct subject (animal). Each row (OTU) is labeled with a predicted taxonomic assignment that is based on the RDP classifier. While the taxonomic identity of some OTUs could be assigned with fairly high resolution, others could be assigned only higher-level identifiers.

Figure 6:
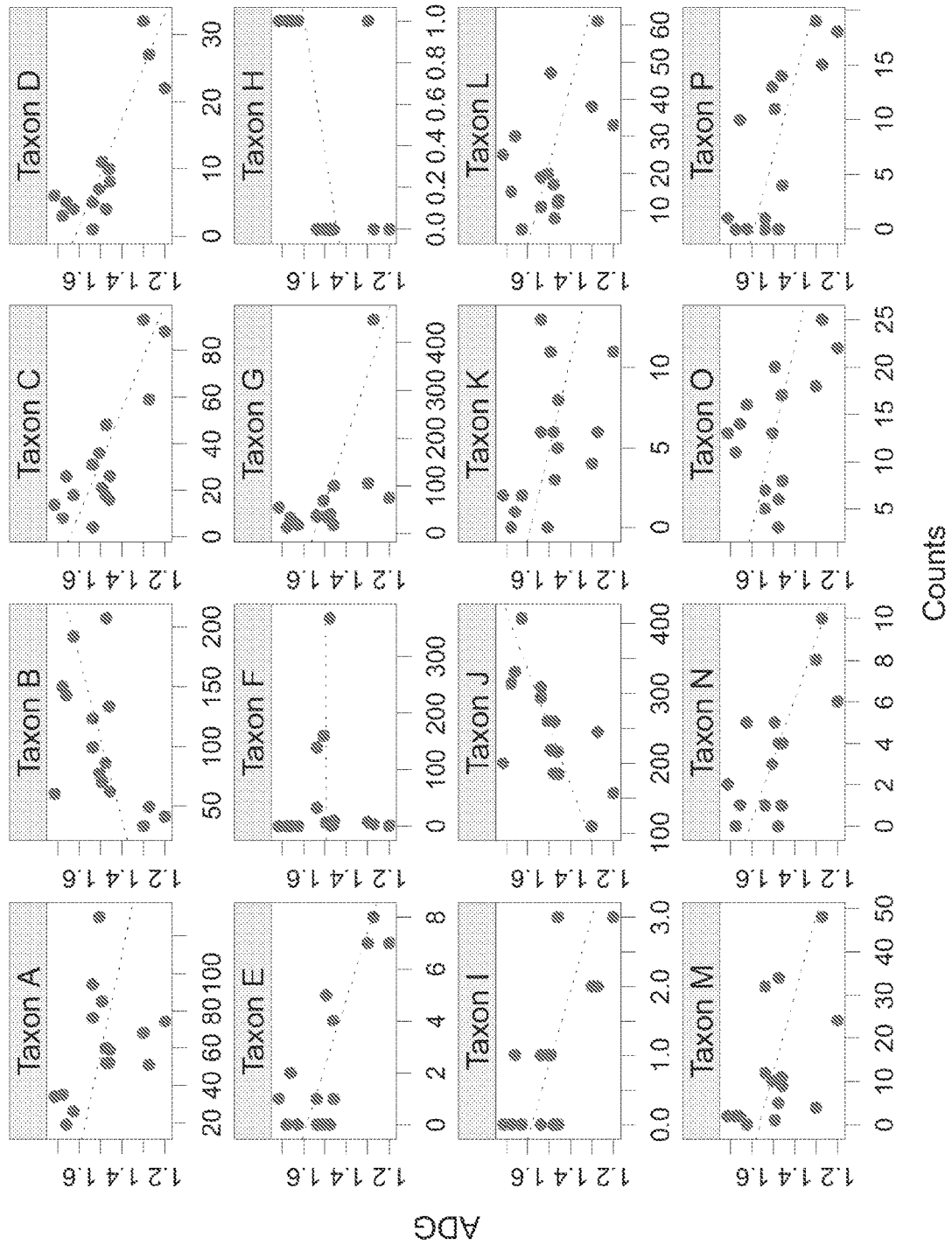
FIG. 6 Scatterplot matrix relating, for each of 15 samples from 11-week-old animals, the absolute abundance (number of 16S amplicon reads out of a rarefied total of 30,000) of each OTU included in the sparse model (x-axis) to the ADG of the animal from which the sequenced sample was derived. For each panel in the scatterplot matrix, a simple linear regression has been applied to the 15 datapoints shown.

FIG. 6, a scatterplot matrix, illustrates that most, if not all, of these 16 features are weak predictors when considered individually. For each of the 16 panels, each blue point denotes the abundance (read counts out of 30,000) of an OTU (x-axis) relative to a subject's ADG (y-axis). Note that the linear correlation between the abundance of any OTU and ADG is generally fairly modest, suggesting that no one feature identified could be used to predict with high accuracy an animal's ADG at 27 weeks of age. Panel titles map to the OTU letter assignments shown in FIG. 5.

Figure 7:
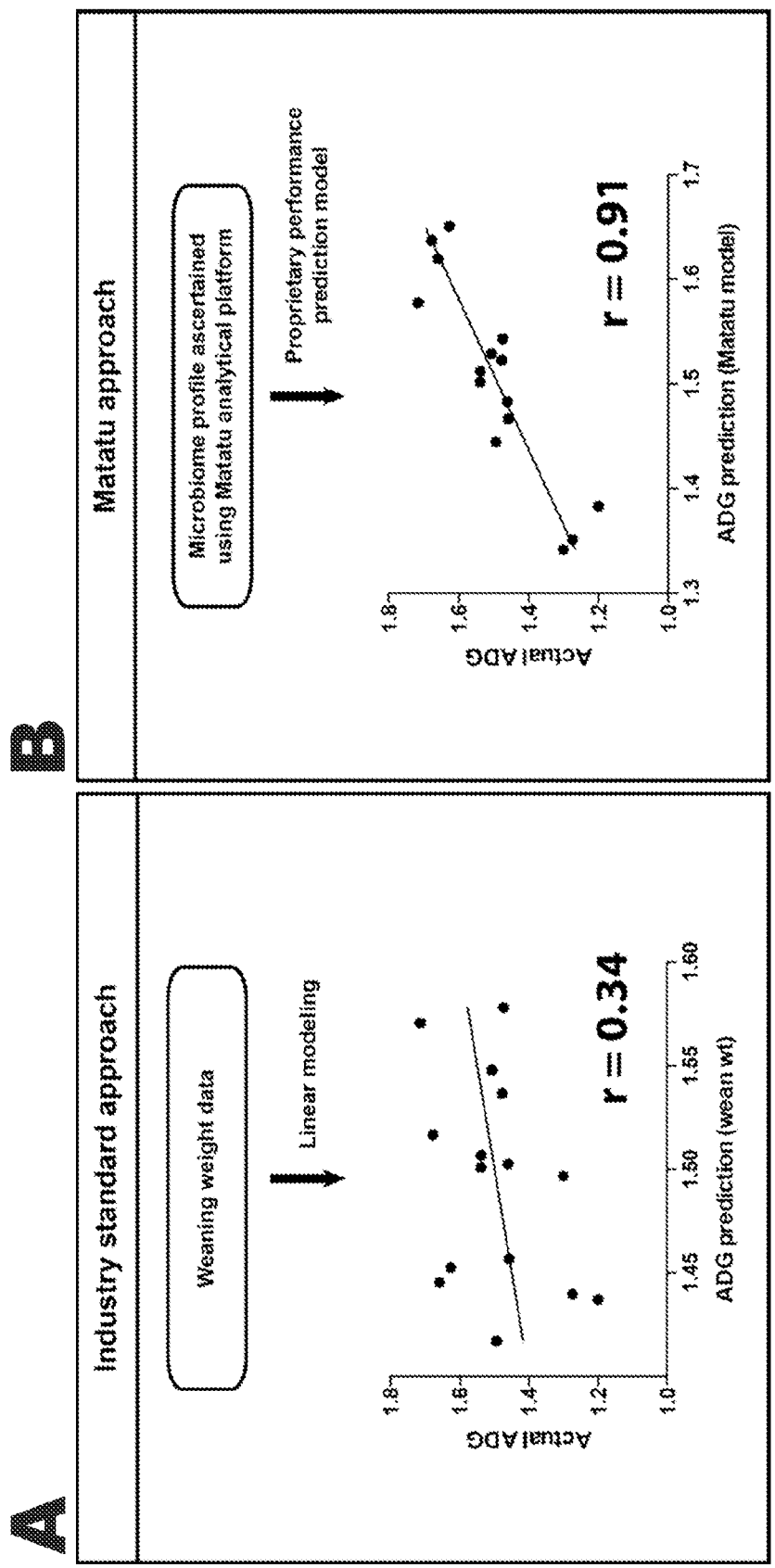
FIG. 7 depicts two prediction models for average daily gain (ADG). On the left, the model uses weaning weight data as an input and linear modeling to predict ADG. On the right, the model uses gut microbial taxonomic information as an input and a learning algorithm to predict ADG. The r values provide a measure of the accuracy of the model, wherein a value closer to 1 is more accurate.

FIG. 7 provides a side-by-side comparison of the extent to which ADG can be predicted based on weaning weight (left panel) versus a predictive model constructed using the system described here with microbial nucleic acid abundance data and known ADGs as training data inputs (right panel). Weaning weight-based predictions are based on a simple linear model in which weaning weight was regressed against ADG for the 11-week-old animals considered in FIG. 5-6. The strength of the linear relationship between the ADG prediction provided by each method and the actual ADG for each animal involved was assessed by calculating Pearson's correlation coefficient.

Example 4

Prediction of Offspring Phenotypes

It is anticipated that the systems and methods of the present technology will also have utility for predicting phenotypes in the offspring of a subject or a plurality of subjects in scenarios where such traits may be influenced at least in part by the activities of bacteria colonizing the body habitats of the subject(s). Such traits would be anticipated to have relatively low heritability vis-à-vis traits driven exclusively by parental genotypes. Heritability can be defined as the percentage of variation in some phenotypic trait due to genetic effects. One example of a phenotypic trait with relatively low heritability in swine is birth weight, whose heritability is often estimated at approximately 20%. To better anticipate the average birth weight of the offspring from a subject animal, someone practicing the present technology would: i) Assemble a first data set using gut microbiota profiles obtained from a number of subjects with characteristics (genetic background, sex, etc.) similar to those of the population targeted for prediction; ii) Assemble a second data set comprising the birth weights of all animals in the same population of subjects assessed in (i); and iii) Use the first and second data sets, with the help of at least one processor, as inputs for a learning application of the type(s) described above to build a model predictive of average live birth weight as a function of maternal microbiota profile. Also note the possibility of including 'additional data sets' as previously described to further improve the performance of such a model. In this illustration, the resulting predictions of future offspring phenotypes would then be used to inform decisions related to the management of pregnant sows and breeding programs. For example, in a scenario where the predicted birth weights of an already pregnant sow are expected to be low, a decision could be made to manage the animal's nutrition, housing, and health status more aggressively than those of other pregnant animals. With regard to breeding programs, such predictions could be very helpful to those deciding which animals are to be bred with one another (in order to maximize live birth weight as one factor in the decision-making process).

What is claimed is:

1. A method for predicting a future characteristic of a particular subject, the method comprising:
   (a) retrieving a first data set and a second data set from a database, wherein:
      (i) the first data set comprises a plurality of microbial nucleic acid features of gut microbiota for each of a plurality of subjects, wherein the microbial nucleic acid features comprise at least one of a qualitative measurement or a quantitative measurement of a first nucleic acid in a nucleic acid sample, and wherein the first nucleic acid comprises a ribosomal gene or a nucleic acid that encodes a polypeptide which can be assigned to a functional group, wherein each of the plurality of subjects are a same species, and there is inter-subject variability in the microbial nucleic acid features;
      (ii) the second data set comprises at least one measurement of a measured characteristic for each of the plurality of subjects and identifies a relationship between the measurement of the measured characteristic and each subject, wherein there is inter-subject variability in the measured characteristic of each subject, and wherein the measured characteristic comprises at least one of a growth and body composition characteristic, a digestive, nutritional, and metabolic characteristic, susceptibility to one or more diseases or a manifestation of disease, an immune characteristics, and a reproductive characteristic;
   (b) processing training data comprising a portion of the first data set and the second data set using a random forest learning algorithm in a classification mode executed by at least one processor to identify a first inter-subject variation in the first data set that impacts a second inter-subject variation in the second data set;
   (c) identifying discriminatory microbial nucleic acid features of gut microbiota that positively or negatively discriminate a characteristic based on the first inter-subject variation identified and the impacted second inter-subject variation;
   (d) defining a predictive model at the at least one processor, the predictive model defining a relationship between the discriminatory microbial nucleic acid features and the characteristic; and
   (e) applying the predictive model to nucleic acid features of the particular subject at the at least one processor to predict at least one particular characteristic of that particular subject, wherein the nucleic acid features of the particular subject comprise at least one of a qualitative measurement or a quantitative measurement of a second nucleic acid, wherein the second nucleic acid comprises the ribosomal gene or the nucleic acid that encodes the polypeptide which can be assigned to the functional group, and wherein the at least one particular characteristic comprises at least one of the growth and body composition characteristic, the digestive, nutritional, and metabolic characteristic, the susceptibility to one or more diseases or a manifestation of disease, the immune characteristics, and the reproductive characteristic;

(f) generating a predictive result, at the at least one processor, for display, the predictive result comprising the at least one particular characteristic for the particular subject; and (g) automatically applying an intervention to the particular subject to address the at least one particular characteristic for the particular subject, wherein the intervention comprises one or more of modifying feed rations, moving the subject to different housing conditions, and administering supplements, medications, or vaccines to the subject.

2. The method of claim 1, wherein the microbial nucleic acid features comprise microbial taxonomic information, microbial functional information, or a combination thereof.

3. The method of claim 2, wherein the microbial taxonomic information is determined from at least about 5,000 sequence reads, and wherein the characteristic is selected from the group consisting of average daily gain, weight, body composition, and feed conversion efficiency.

4. The method of claim 1, wherein the database further comprises an additional data set, the additional data set comprising an additional characteristic measurement for each subject included in the first data set; and the learning application processes the first data set, the second data set and the additional data set to identify inter-subject variation in the microbial nucleic acid features of the first data set and the additional data set that relate to inter-subject variation in the at least one measurement of the measured characteristic in the second data set.

5. The method of claim 1, wherein at least one of the microbial nucleic acid features is microbial taxonomic information.

6. The method of claim 1, wherein the at least one particular characteristic is selected from the group consisting of average daily gain, weight, and feed conversion efficiency, wherein the gut microbiota sample is a fecal sample, wherein the subjects are swine, wherein the microbial nucleic acid features are a group of at least three OTUs, wherein step (a) of claim 1 further comprises retrieving an additional data set from a database, the additional data set comprising an additional characteristic measurement for each subject included in the first data set; and step (b) of claim 1 further comprises processing the first data set, the second data set and the additional data set to identify inter-subject variation in the microbial nucleic acid features of the first data set and the additional data set that relate to inter-subject variation in the at least one measurement of the measured characteristic in the second data set.

7. The method of claim 1, wherein the at least one particular characteristic relates to performance of the offspring of the subject.

8. The method of claim 1, further comprising determining a breeding index.

9. The method of claim 1, wherein the at least one particular characteristic relates to performance of the offspring of the plurality of subjects, and wherein offspring performance relates to growth and body composition characteristics of the offspring.

10. The method of claim 9, wherein the growth and body composition characteristics of the offspring comprise one or more of digestive characteristics, nutritional characteristics, metabolic characteristics, susceptibility to one or more diseases and the manifestations of a disease, immune characteristics, reproductive characteristics, height, weight, length, girth, lean body mass, average daily gain (ADG) in height, ADG in weight, ADG in length, ADG in girth, finishing weight, carcass weight, carcass muscling, carcass cutability, pattern of fat deposition, meat quality, feed conversion ratio, feed efficiency, nutrient utilization from feed, blood glucose concentration, blood triglyceride concentration, and serum IGF-1 concentration of the offspring.

11. The method of claim 9, wherein the growth and body composition characteristics of the offspring comprise one or more of disease duration, disease severity, disease frequency, morbidity, mortality, resistance to disease, susceptibility to disease, response to vaccination, pathogen specific antibody count, and gut inflammation in the offspring.

12. The method of claim 10, wherein the reproductive characteristics comprise one or more of litter size, frequency of still born births, and average litter birth weight.

13. The method of claim 1, wherein the at least one particular characteristic comprises at least one of an average daily gain in one or more of height, weight, length, or girth, and wherein the intervention comprises modifying feed rations.

14. The method of claim 1, wherein the at least one particular characteristic comprises at least one of a feed conversion ratio or a feed efficiency, and wherein the intervention comprises modifying feed rations.

* * * * *